United States Patent
Chang et al.

(10) Patent No.: US 12,236,596 B2
(45) Date of Patent: Feb. 25, 2025

(54) APPARATUS AND METHOD FOR PROCESSING IMAGE

(71) Applicant: Korea Advanced Institute Of Science and Technology, Daejeon (KR)

(72) Inventors: JaeByum Chang, Daejeon (KR); Hyunwoo Kim, Daejeon (KR); Junyoung Seo, Daejeon (KR); Young-Gyu Yoon, Daejeon (KR); Hoyeon Nam, Daejeon (KR); Seoungbin Bae, Daejeon (KR); Junmo Cho, Daejeon (KR)

(73) Assignee: Korea Advanced Institute Of Science And Technology, Daejeon (KR)

(*) Notice: Subject to any disclaimer, the term of this patent is extended or adjusted under 35 U.S.C. 154(b) by 0 days.

(21) Appl. No.: 18/602,661

(22) Filed: Mar. 12, 2024

(65) Prior Publication Data

US 2024/0257346 A1 Aug. 1, 2024

Related U.S. Application Data

(63) Continuation of application No. PCT/KR2022/013762, filed on Sep. 15, 2022.

(30) Foreign Application Priority Data

Sep. 16, 2021 (KR) .................. 10-2021-0123583
Sep. 2, 2022 (KR) .................. 10-2022-0111591

(51) Int. Cl.
*G06T 7/00* (2017.01)
(52) U.S. Cl.
CPC .. *G06T 7/0012* (2013.01); *G06T 2207/10064* (2013.01); *G06T 2207/20081* (2013.01); *G06T 2207/20084* (2013.01)

(58) Field of Classification Search
CPC ......... G06T 2207/30024; G06T 7/0012; G06T 2207/10056; G06T 2207/20212;
(Continued)

(56) References Cited

U.S. PATENT DOCUMENTS 9,607,374 B2 * 3/2017 Azar .................. G06T 7/0012
10,275,880 B2 * 4/2019 Barnes .................. G06T 7/11
(Continued)

FOREIGN PATENT DOCUMENTS

| KR | 1020200031687 A | | 3/2020 | |
|---|---|---|---|---|
| KR | 20210087869 A | * | 7/2021 | ......... G01N 21/6428 |
| KR | 1020210087869 A | | 7/2021 | |

OTHER PUBLICATIONS

Machine translation of KR20210087869A obtained from Google Patents (Year: 2021).*

(Continued)

*Primary Examiner* — Aaron W Carter
*Assistant Examiner* — Courtney Joan Nelson
(74) *Attorney, Agent, or Firm* — Nixon Peabody LLP

(57) ABSTRACT

As an aspect of the present disclosure, a method of processing an image may be proposed. The method is a method of processing an image, which is performed by an electronic device including one or more processors and one or more memories in which instructions to be executed by the one or more processors are stored, and may include obtaining a first mixed image of a sample including a first biomolecule labeled with a first fluorescent material and a second biomolecule that has not been labeled, obtaining a second mixed image of the sample including the first biomolecule labeled with the first fluorescent material and the second biomolecule labeled with a second fluorescent material, and generating an unmixed image of the second biomolecule based on the first mixed image and the second mixed image.

19 Claims, 16 Drawing Sheets

(58) Field of Classification Search
CPC .............. G06T 5/50; G06T 2207/10064; G06T 2207/20081; G06T 2207/20084; G06V 20/695; G06V 20/69; G01N 1/30; G01N 2021/6441; G01N 21/6428; G01N 21/6458; G01N 2001/302; G01N 33/582; G01N 21/6456; A61B 5/0075; A61B 5/145

See application file for complete search history.

(56) References Cited

U.S. PATENT DOCUMENTS

| | | | | |
|---|---|---|---|---|
| 10,761,027 B2* | 9/2020 | Yoshihara | ............ | G06V 20/698 |
| 10,839,509 B2* | 11/2020 | Goodman | ............ | G06T 7/0012 |
| 11,257,301 B2 | 2/2022 | Tominaga | | |
| 2020/0184192 A1* | 6/2020 | Tominaga | ............ | G06V 10/46 |
| 2020/0226462 A1* | 7/2020 | Maddison | ............ | G01N 33/53 |
| 2021/0208076 A1 | 7/2021 | Chang | | |

OTHER PUBLICATIONS

Seo, Junyoung, et al. "PICASSO: Ultra-multiplexed fluorescence imaging of biomolecules through single-round imaging and blind source unmixing." BioRxiv (2021): Jan. 2021. (Year: 2021).*

Radtke et al. "IBEX: A versatile multiplex optical imaging approach for deep phenotyping and spatial analysis of cells in complex tissues." Proceedings of the National Academy of Sciences 117.52, Nov. 11, 2020, 33455-33465.

Seo et al. "PICASSO: Ultra-multiplexed fluorescence imaging of biomolecules through single-round imaging and blind source unmixing" BioRxiv [online], Jan. 27, 2021, Retrieved from the internet: [URL: https://www.biorxiv.org/content/10.1101/2021.01.27.428247v1.full.pdf].

International Search Report issued in PCT/KR2022/013762 on Dec. 22, 2022.

* cited by examiner

APPARATUS AND METHOD FOR PROCESSING IMAGE

CROSS-REFERENCES TO RELATED APPLICATIONS

This application is a bypass continuation application of PCT International Application PCT/KR2022/013762, which has an International filing date of Sep. 15, 2022, and claims priorities to Korean Patent Application No. 10-2021-0123583, filed on Sep. 16, 2021, and Korean Patent Application No. 10-2022-0111591, filed on Sep. 2, 2022 in the Korean intellectual property office, the disclosures of which are herein incorporated by reference in their entireties.

TECHNICAL FIELD

The present disclosure relates to a technology for processing an image.

BACKGROUND OF THE DISCLOSURE

A fluorescent imaging scheme for a biological sample is a scheme capable of indirectly monitoring a biological material within a sample by labeling, using fluorescent material, a biomolecule included in the sample and then photographing light emitted from the fluorescent material. When the light is radiated to fluorescent materials, they absorb the light, become excited, and then emit light. In this case, the fluorescent materials emit light of a longer wavelength than the absorbed light. For example, fluorescent materials absorb light of a specific wavelength band (e.g., 350 to 400 nm) and emit light of a specific wavelength band (e.g., 400 to 600 nm). In this case, a degree that the fluorescent materials are excited for each wavelength is indicated as an excitation spectrum. The intensity of light emitted for each wavelength is indicated as an emission spectrum.

According to a conventional technology, in order to monitor a plurality of biomolecules included in a sample, there are restrictions that emission spectra should not be overlapped as much as possible. Accordingly, there are restrictions that the number of fluorescent materials which may be simultaneously monitored is limited.

SUMMARY

The present disclosure provides a technology for processing an image.

As an aspect of the present disclosure, a method of processing an image may be proposed. The method is a method of processing an image, which is performed by an electronic device including one or more processors and one or more memories in which instructions to be executed by the one or more processors are stored, and may include obtaining a first mixed image of a sample including a first biomolecule labeled with a first fluorescent material and a second biomolecule that has not been labeled, obtaining a second mixed image of the sample including the first biomolecule labeled with the first fluorescent material and the second biomolecule labeled with a second fluorescent material, and generating an unmixed image of the second biomolecule based on the first mixed image and the second mixed image.

In an embodiment, the first mixed image and the second mixed image may be images photographed by detecting light of the same specific wavelength band from the sample.

In an embodiment, the first mixed image and the second mixed image may be images obtained based on the same emission filter, and the emission filter may be a filter that transmits light of a specific wavelength band.

In an embodiment, the first fluorescent material and the second fluorescent material may be the same fluorescent material.

In an embodiment, the first fluorescent material and the second fluorescent material may be determined so that a first wavelength value at which the first fluorescent material's emission signal intensity becomes a maximum within an emission spectrum of the first fluorescent material and a second wavelength value at which the second fluorescent material's emission signal intensity becomes a maximum within an emission spectrum of the second fluorescent material satisfy a given condition.

In an embodiment, the given condition may be a condition that is satisfied when a difference value between the first wavelength value and the second wavelength value is a predetermined threshold value or less.

In an embodiment, the given condition may be a condition that is satisfied when a ratio of a smaller wavelength value to a greater wavelength value, among the first wavelength value and the second wavelength value, is a predetermined threshold ratio or more.

In an embodiment, the second mixed image may be obtained by staining the second biomolecule included in the sample with the second fluorescent material and then photographing the sample, after the first mixed image of the sample is photographed.

In an embodiment, the generating of the unmixed image may include processing the first mixed image and the second mixed image by using an unmixing matrix.

In an embodiment, a value of at least one element of the unmixing matrix may be determined based on a trained artificial neural network model.

In an embodiment, the method may further include obtaining a third mixed image of the sample including the first biomolecule labeled with the first fluorescent material, the second biomolecule labeled with the second fluorescent material, and a third biomolecule labeled with a third fluorescent material. The generating of the unmixed image may include generating an unmixed image of the third biomolecule additionally based on the third mixed image. The first mixed image may be an image obtained by photographing the sample including the second biomolecule that has not been labeled and the third biomolecule that has not been labeled. The second mixed image may be an image obtained by photographing the sample including the third biomolecule that has not been labeled.

In an embodiment, the second mixed image may be obtained by staining the second biomolecule included in the sample with the second fluorescent material and then photographing the sample, after the first mixed image of the sample is photographed. The third mixed image may be obtained by staining the third biomolecule included in the sample with the third fluorescent material and then photographing the sample, after the second mixed image of the sample is photographed.

According to another aspect of the present disclosure, an electronic device for image processing may be proposed. The electronic device may include one or more processors and one or more memories in which instructions to be executed by the one or more processors are stored. The one or more processors may obtain a first mixed image of a sample including a first biomolecule labeled with a first fluorescent material and a second biomolecule that has not been labeled, may obtain a second mixed image of the sample including the first biomolecule labeled with the first fluorescent material and the second biomolecule labeled with a second fluorescent material, and may generate an unmixed image of the second biomolecule based on the first mixed image and the second mixed image.

In an embodiment, the first mixed image and the second mixed image may be images photographed by detecting light of the same specific wavelength band from the sample.

In an embodiment, the first mixed image and the second mixed image may be images obtained based on the same emission filter. The emission filter may be a filter that transmits light of a specific wavelength band.

In an embodiment, the first fluorescent material and the second fluorescent material may be the same fluorescent material.

In an embodiment, the first fluorescent material and the second fluorescent material may be determined so that a first wavelength value at which an intensity of the first fluorescent material's emission signal becomes a maximum within an emission spectrum of the first fluorescent material and a second wavelength value at which the intensity of the second fluorescent material's emission signal becomes a maximum within an emission spectrum of the second fluorescent material satisfy a given condition.

In an embodiment, the second mixed image may be obtained by staining the second biomolecule included in the sample with the second fluorescent material and then photographing the sample, after the first mixed image of the sample is photographed.

In an embodiment, the electronic device may further include a photographing unit. The one or more processors may obtain the first mixed image by photographing the sample including the first biomolecule labeled with the first fluorescent material and the second biomolecule that has not been labeled through the photographing unit, and may obtain the second mixed image by photographing the sample including the first biomolecule labeled with the first fluorescent material and the second biomolecule labeled with the second fluorescent material through the photographing unit.

In an embodiment, the one or more processors may generate the unmixed image based on a dependence evaluation value that is calculated between the first mixed image and the second mixed image.

In an embodiment, the dependence evaluation value may be at least one of mutual information, a Kullback-Leibler divergence value, a Cross entropy value, or a Rand index.

In an embodiment, the one or more processors may generate the unmixed image, based on an output value that is calculated based on the first mixed image and the second mixed image by a trained artificial neural network.

As still another aspect of the present disclosure, a non-transitory computer-readable recording medium on which instructions for image processing have been recorded may be proposed. In a non-transitory computer-readable recording medium on which upon execution by one or more processors, instructions enabling the one or more processors to perform an operation are recorded, the instructions may enable the one or more processors to obtain a first mixed image of a sample including a first biomolecule labeled with a first fluorescent material and a second biomolecule that has not been labeled, obtain a second mixed image of the sample including the first biomolecule labeled with the first fluorescent material and the second biomolecule labeled with a second fluorescent material, and generate an unmixed image of the second biomolecule based on the first mixed image and the second mixed image.

The method of processing an image according to the present disclosure can reduce the time taken for image processing because it does not require a process of inactivating or removing a fluorescent material, which is required by a conventional method.

DETAILED DESCRIPTION

Figure 1:
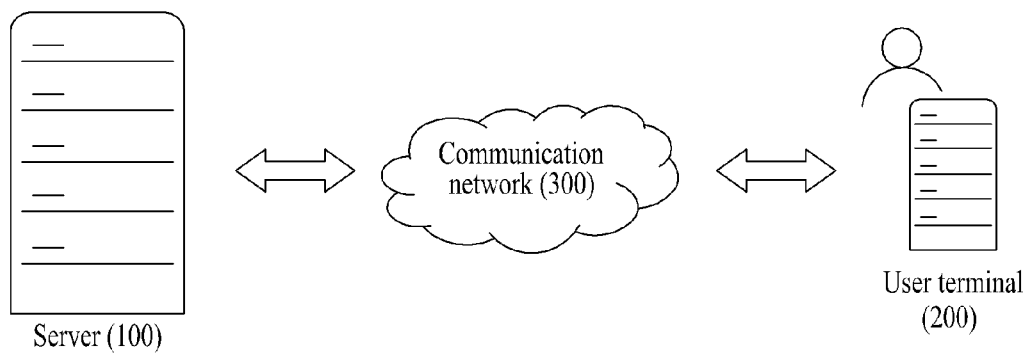
FIG. 1 is a diagram illustrating a system including a server, a user terminal, and a communication network according to an embodiment of the present disclosure.

Various embodiments described in this document have been exemplified for purposes of clearly describing the technical spirit of the present disclosure, and are not intended to limit the technical spirit of the present disclosure to a specific embodiment. The technical spirit of the present disclosure includes various modifications, equivalents, and alternatives of each embodiment described in this document and an embodiment selectively combined from all or some of each embodiment. Furthermore, the scope of rights of the technical spirit of the present disclosure is not limited to the following various embodiments or detailed descriptions thereof.

Terms used in this document, including technical or scientific terms, may have meanings that are commonly understood by a person having ordinary knowledge in the technical field to which the present disclosure pertains unless defined otherwise.

Expressions, such as "include", "may include", "equipped with", "may be equipped with", "have", and "may have" which are used in this document, mean the presence of a targeted characteristic (e.g., a function, an operation, or a component), and do not exclude the presence of another additional characteristic. That is, such expressions should be understood as open-ended terms that connote the possibility that another embodiment will be included.

An expression of the singular number used in this document may include the meaning of the plural number unless described otherwise in the context, which is also likewise applied to an expression of the singular number written in the claims.

An expression, such as "a first", "a second", "the first", or "the second" used in this document, is used to distinguish one target from another target in denoting a plurality of heterogeneous targets unless described otherwise in the context, and does not limit an order or importance between corresponding targets. For example, a plurality of fluorescent materials according to the present disclosure may be distinguished from one another by expressing the fluorescent materials like a "first fluorescent material" and a "second fluorescent material." Furthermore, a plurality of input images according to the present disclosure may be distinguished from one another by expressing the input images like a "first input image" and a "second input image." Likewise, terms used in the present disclosure, such as a "biomolecule", an "unmixed image", and "a probability distribution", may be distinguished from one another by expressions, such as "a first" and "a second."

An expression, such as "A, B, and C," "A, B, or C," "at least one of A, B, and C", or "at least one of A, B, or C" used in this document, may mean each listed item or all possible combinations of listed items. For example, "at least one of A or B" may denote all of (1) at least one A, (2) at least one B, (3) at least one A, and at least one B.

An expression "unit" used in this document may mean software or a hardware component, such a field-programmable gate array (FPGA) or an application specific integrated circuit (ASIC). However, the "unit" is not limited to hardware and software. The "unit" may be constructed to be stored in an addressable storage medium or may be constructed to execute one or more processors. In an embodiment, the "unit" may include components, such as software components, object-oriented software components, class components, and task components, a processor, a function, attributes, a procedure, a subroutine, a segment of a program code, a driver, firmware, a microcode, a circuit, data, a database, a data structure, a table, an array, and a variable.

An expression "based on~" used in this document is used to describe one or more factors that are described in a phrase or sentence including a corresponding expression and that affect a behavior or operation of a determination or decision. The expression does not exclude an additional factor that affects a behavior or operation of a corresponding determination or decision.

An expression that a component (e.g., a first component) is "connected" or "coupled" to another component (e.g., a second component) used in this document may mean that the component is directly connected or coupled to the another component and may also mean that the component is connected or coupled to the another component through the medium of another new component (e.g., a third component).

An expression "configured to ~" used in this document may have a meaning, such as "set to ~", "have the ability to ~", "changed to ~", "produced to ~", or "may ~" depending on context. The corresponding expression is not limited to a meaning "specially designed in hardware." For example, a processor configured to perform a specific operation may mean a generic purpose processor capable of performing a specific operation by executing software or may mean a special purpose computer that has been structured through programming to perform the corresponding specific operation.

In the present disclosure, artificial intelligence (AI) means a technology for imitating the learning ability, inference ability, and perception ability of the human being and implementing the imitated abilities through a computer, and may include machine learning and the concept of symbolic logic. Machine learning (ML) may be an algorithm technology for autonomously classifying and learning characteristics of input data. The technology of AI is an algorithm of machine learning, and may analyze input data, may learn the results of the analysis, and may perform a determination or prediction based on the results of the learning. Furthermore, technologies for imitating the perception and determination functions of the human brain by using the algorithm of machine learning may also be understood as being the category of AI. For example, the technologies may include technical fields, such as linguistic understanding, visual understanding, reasoning/prediction, knowledge representation, and behavior control.

In the present disclosure, machine learning may mean processing for training a neural network model by using experiences of data processing, and may mean that computer software autonomously improves the data processing ability through the machine learning. The neural network model has been constructed by modeling a correlation between data, and the correlation may be represented by a plurality of parameters. The artificial neural network model derives the correlation between data by extracting and analyzing features from given data. Optimizing a parameter of the neural network model by repeating such a process may be said to be the machine learning. For example, an artificial neural network model may learn mapping (correlation) between an input and an output with respect to data given as an input and output pair. Alternatively, the artificial neural network model may learn a correlation between input data by deriving regularity between given data, even when only the input data is given.

In the present disclosure, an artificial neural network, an AI learning model, a machine learning model, or an artificial neural network model may be designed to implement the brain structure of the human being on a computer, and may include a plurality of network nodes that imitate a neuron of a neural network of the human being and have weights. The plurality of network nodes may imitate the synaptic activities of neurons that exchange signals through a synapse, and may have a connection relation therebetween. In the artificial neural network, a plurality of network nodes is disposed at layers having different depths, and may exchange data based on a convolution connection relation. The artificial neural network may be an artificial neural network model or a convolution neural network model, for example.

Hereinafter, various embodiments of the present disclosure are described with reference to the accompanying drawings. In the accompanying drawings and the description of the accompanying drawings, the same or substantially equivalent component may be assigned the same reference numeral. Furthermore, in the description of various embodiments below, redundantly describing the same or corresponding component may be omitted, but this does not mean that a corresponding component is not included in a corresponding embodiment.

FIG. 1 is a diagram illustrating a system including a server 100, a user terminal 200, and a communication network 300 according to an embodiment of the present disclosure. The server 100 and the user terminal 200 may exchange information over the communication network 300.

The server 100 may be an electronic device that performs an image processing operation according to the present disclosure. The server 100 is an electronic device that transmits information or the results of image processing to the user terminal 200 connected thereto in a wired or wireless way, and may be an application server, a proxy server, or a cloud server, for example.

The user terminal 200 may be a terminal of a user who wants to receive the results of image processing. The user terminal 200 may be at least one of a smartphone, a tablet computer, a personal computer (PC), a mobile phone, personal digital assistants (PDA), an audio player, and a wearable device, for example. The communication network 300 may include both wired and wireless communication networks.

The communication network 300 may enable data to be exchanged between the server 100 and the user terminal 200. A wired communication network may include a communication network using a method, such as a universal serial bus (USB), a high definition multimedia interface (HDMI), recommended standard-232 (RS-232), or plain old telephone service (POTS), for example. A wireless communication network may include a communication network using a method, such as an enhanced mobile broadband (eMBB), ultra reliable low-latency communications (URLLC), massive machine type communications (MMTC), long-term evolution (LTE), LTE advance (LTE-A), a new radio (NR), a universal mobile telecommunications system (UMTS), global system for mobile communications (GSM), code division multiple access (CDMA), wideband CDMA (WCDMA), a wireless broadband (WiBro), wireless fidelity (WIFI), Bluetooth, near field communication (NFC), a global positioning system (GPS), or a global navigation satellite system (GNSS), for example. In this specification, the communication network 300 is not limited to the aforementioned examples, and may include various types of communication networks that enable data to be exchanged between a plurality of subjects or devices without restriction.

When the construction or operation of one device is described in the disclosed contents of this specification, a term "device" may be used as a term for denoting a device, that is, the subject of description. A term "external device" may be used as a term for denoting a device that is present in the outside when viewed from a viewpoint of a device, that is, the subject of description. For example, if the server 100 is set and described as a "device", the user terminal 200 may be called an "external device" from a viewpoint of the server 100. Furthermore, for example, if the user terminal 200 is set and described as a "device", the server 100 may be called an "external device" from a viewpoint of the user terminal 200. That is, the server 100 and the user terminal 200 may be denoted as a "device" and an "external device", respectively, or may be denoted as an "external device" and a "device", respectively, depending on the viewpoint of the subject of an operation.

Figure 2:
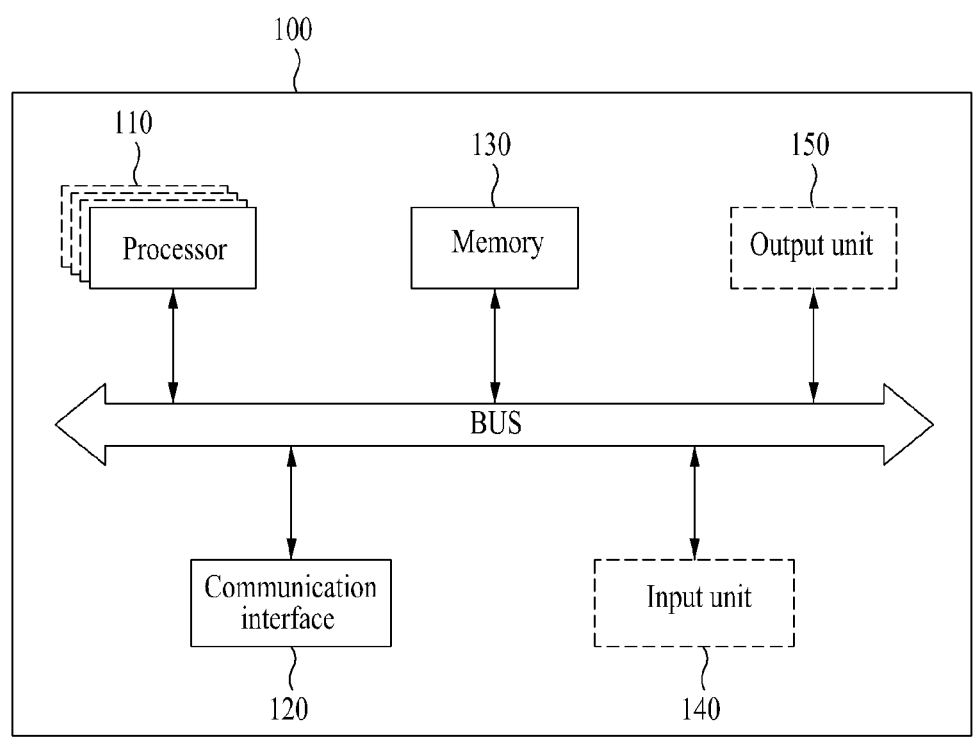
FIG. 2 is a block diagram of the server according to an embodiment disclosed in this specification.

FIG. 2 is a block diagram of the server 100 according to an embodiment disclosed in this specification. The server 100 may include one or more processors 110, a communication interface 120, or a memory 130 as a component. In an embodiment, at least one of the components of the server 100 may be omitted or another component may be added to the server 100. In an embodiment, additionally or alternatively (in alternative to), some components of the server 100 may be integrated and implemented or may be implemented as one or a plurality of entities. At least some of components inside or outside the server 100 may exchange data or signals by being interconnected through a bus, general purpose input/output (GPIO), a serial peripheral interface (SPI), or a mobile industry processor interface (MIPI).

The one or more processors 110 may be represented as a processor 110. The term "processor 110" may mean a set of one or more processors unless clearly expressed otherwise in the context. The processor 110 may control at least one component of the server 100 connected to the processor 110 by driving software (e.g., an instruction or a program). Furthermore, the processor 110 may perform an operation, such as various operations, processing, data generation, or processing. Furthermore, the processor 110 may load data from the memory 130 or may store data in the memory 130.

The communication interface 120 may perform wireless or wired communication between the server 100 and another device (e.g., the user terminal 200 or another server). For example, the communication interface 120 may perform wireless communication according to a method, such as eMBB, URLLC, MMTC, LTE, LTE-A, NR, UMTS, GSM, CDMA, WCDMA, WiBro, WiFi, Bluetooth, NFC, GPS, or GNSS. Furthermore, for example, the communication interface 120 may perform wired communication according to a method, such as a USB, HDMI, RS-232, or POTS.

The memory 130 may store various data. Data stored in the memory 130 is data that is obtained, processed, or used by at least one component of the server 100, and may include software (e.g., an instruction or a program). The memory 130 may include a volatile or nonvolatile memory. The term "memory 130" may mean a set of one or more memories unless clearly expressed otherwise in the context. An expression "a set of instructions stored in the memory 130" or "a program stored in the memory 130" described in this specification may be used to denote middleware that provides an application with various functions so that an operating system, an application, or an application for controlling a resource of the server 100 can use resources of the server 100. In an embodiment, when the processor 110 performs a specific operation, the memory 130 may store instructions that are performed by the processor 110 and that correspond to a specific operation.

In an embodiment, the server 100 may transmit, to an external device, data according to operation results of the processor 110, data received by the communication interface 120, or data stored in the memory 130. The external device may be a device for showing, displaying, or outputting received data.

In an embodiment, the server 100 may further include an input unit 140. The input unit 140 may be a component for delivering data received from the outside to at least one component included in the server 100. For example, the input unit 140 may include at least one of a mouse, a keyboard, or a touch pad.

In an embodiment, the server 100 may further include an output unit 150. The output unit 150 may display (or output) information processed by the server 100 or may transmit (or deliver) the information. For example, the output unit 150 may visually display information processed by the server 100. The output unit 150 may display user interface (UI) information or graphic user interface (GUI) information. In this case, the output unit 150 may include at least one of a liquid crystal display (LCD), a thin film transistor-liquid crystal display (TFT-LCD), an organic light-emitting diode (OLED), a flexible display, a 3D display, and E-ink display. Furthermore, for example, the output unit 150 may acoustically display information processed by the server 100. The output unit 150 may display audio data according to a given audio file format (e.g., MP3, FLAC, or WAV) method through an acoustic device. In this case, the output unit 150 may include at least one of a speaker, a headset, and a headphone. Furthermore, for example, the output unit 150 may transmit, to an external output device, information processed by the server 100. The output unit 150 may transmit or deliver, to an external output device, information processed by the server 100 by using the communication interface 120. The output unit 150 may transmit or deliver, to an external output device, information processed by the server 100 by using a separate communication interface for an output.

In an embodiment, the server 100 may further include a photographing unit (not illustrated). The photographing unit may be a camera or a camera that includes a microscope device, for example. The processor 110 may photograph an image of a target (e.g., a sample) and obtain a photographed image by controlling the photographing unit, and may store the image in the memory 130. Alternatively, if the server 100 includes the output unit 150, the processor 110 may photograph an image of a target by controlling the photographing unit, and may display the photographed image on the output unit 150. In another embodiment, the server 100 may obtain a photographed image from an external photographing device.

Figure 3:
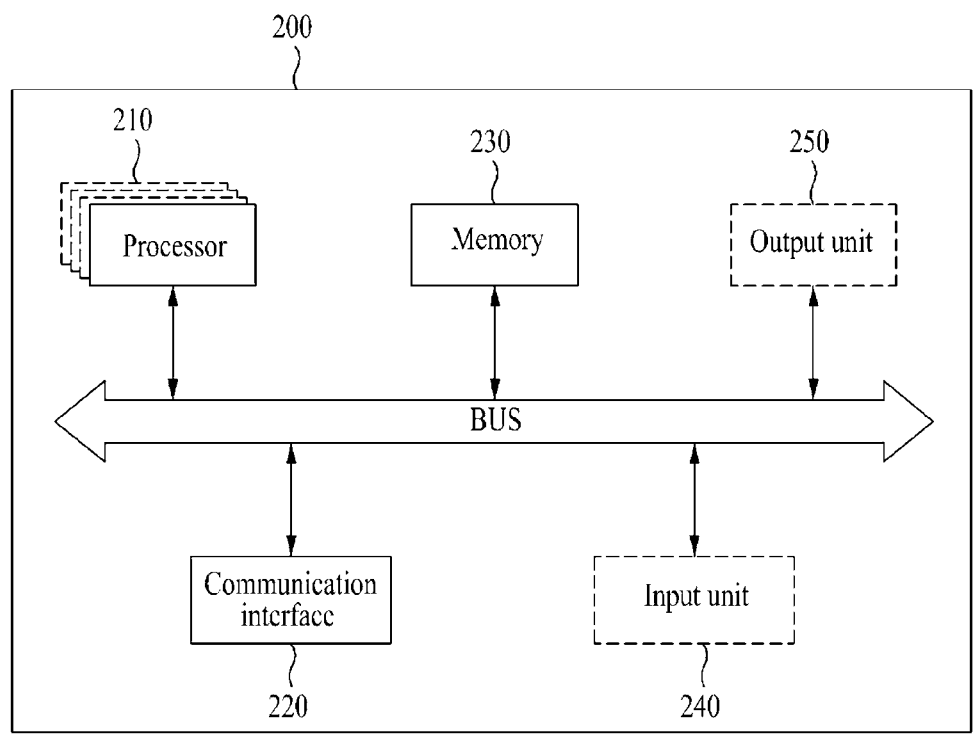
FIG. 3 is a block diagram of the user terminal according to an embodiment disclosed in this specification.

FIG. 3 is a block diagram of the user terminal 200 according to an embodiment disclosed in this specification. The user terminal 200 may include one or more processors 210, a communication interface 220, or a memory 230 as a component. Furthermore, the user terminal 200 may further include at least one of an input unit 240 or an output unit 250.

The processor 210 may control at least one component of the user terminal 200 connected to the processor 210 by driving software (e.g., an instruction or a program). Furthermore, the processor 210 may perform an operation, such as various operations, processing, data generation, or processing. Furthermore, the processor 210 may load data from the memory 230 or may store data in the memory 230.

The communication interface 220 may perform wireless or wired communication between the user terminal 200 and another device (e.g., the server 100 or another user terminal). For example, the communication interface 220 may perform wireless communication according to a method, such as eMBB, URLLC, MMTC, LTE, LTE-A, NR, UMTS, GSM, CDMA, WCDMA, WiBro, WiFi, Bluetooth, NFC, GPS, or GNSS. Furthermore, for example, the communication interface 220 may perform wired communication according to a method, such as a USB, HDMI, RS-232, or POTS.

The memory 230 may store various data. Data stored in the memory 230 is data that is obtained, processed, or used by at least one component of the user terminal 200, and may include software (e.g., an instruction or a program). The memory 230 may include a volatile or nonvolatile memory. The term "memory 230" may mean a set of one or more memories unless clearly expressed otherwise in the context. An expression "a set of instructions stored in the memory 230" or "a program stored in the memory 230" described in this specification may be used to denote an operating system for controlling a resource of the user terminal 200, an application, or a middleware that provides an application with various functions so that the application can use resources of the user terminal 200. In an embodiment, when the processor 210 performs a specific operation, the memory 230 may store instructions that are performed by the processor 210 and that correspond to a specific operation.

In an embodiment, the user terminal 200 may further include an input unit 240. The input unit 240 may be a component for delivering data received from the outside to at least one component included in the user terminal 200. For example, the input unit 240 may include at least one of a mouse, a keyboard, or a touch pad.

In an embodiment, the user terminal 200 may further include an output unit 250. The output unit 250 may display (or output) information processed by the user terminal 200 or may transmit (or deliver) the information. For example, the output unit 250 may visually display information processed by the user terminal 200. The output unit 250 may display user interface (UI) information or graphic user interface (GUI) information. In this case, the output unit 250 may include at least one of a liquid crystal display (LCD), a thin film transistor-liquid crystal display (TFT-LCD), an organic light-emitting diode (OLED), a flexible display, a 3D display, and E-ink display. Furthermore, for example, the output unit 250 may acoustically display information processed by the user terminal 200. The output unit 250 may display audio data according to a given audio file format (e.g., MP3, FLAC, or WAV) method through an acoustic device. In this case, the output unit 250 may include at least one of a speaker, a headset, and a headphone. Furthermore, for example, the output unit 250 may transmit, to an external output device, information processed by the user terminal 200. The output unit 250 may transmit or deliver, to an external output device, information processed by the user terminal 200 by using the communication interface 220. The output unit 250 may transmit or deliver, to an external output device, information processed by the user terminal 200 by using a separate communication interface for an output.

In an embodiment, the user terminal 200 may further include a photographing unit (not illustrated). The photographing unit may be a camera or a camera that includes a microscope device, for example. The processor 210 may photograph an image of a target (e.g., a sample) and obtain a photographed image by controlling the photographing unit, and may store the image in the memory 230. The user terminal 200 may display a photographed image on the output unit 250. The user terminal 200 may transmit a photographed image to the server 100. Furthermore, the user terminal 200 may obtain a photographed image from an external photographing device.

In the following description, for convenience of description, the subject of an operation may be omitted. In this case, it may be understood that each operation is performed by the server 100. However, a method according to the present disclosure may be performed by the user terminal 200, and some of operations included in the method may be performed by the user terminal 200 and the remaining operations may be performed by the server 100.

Figure 4:
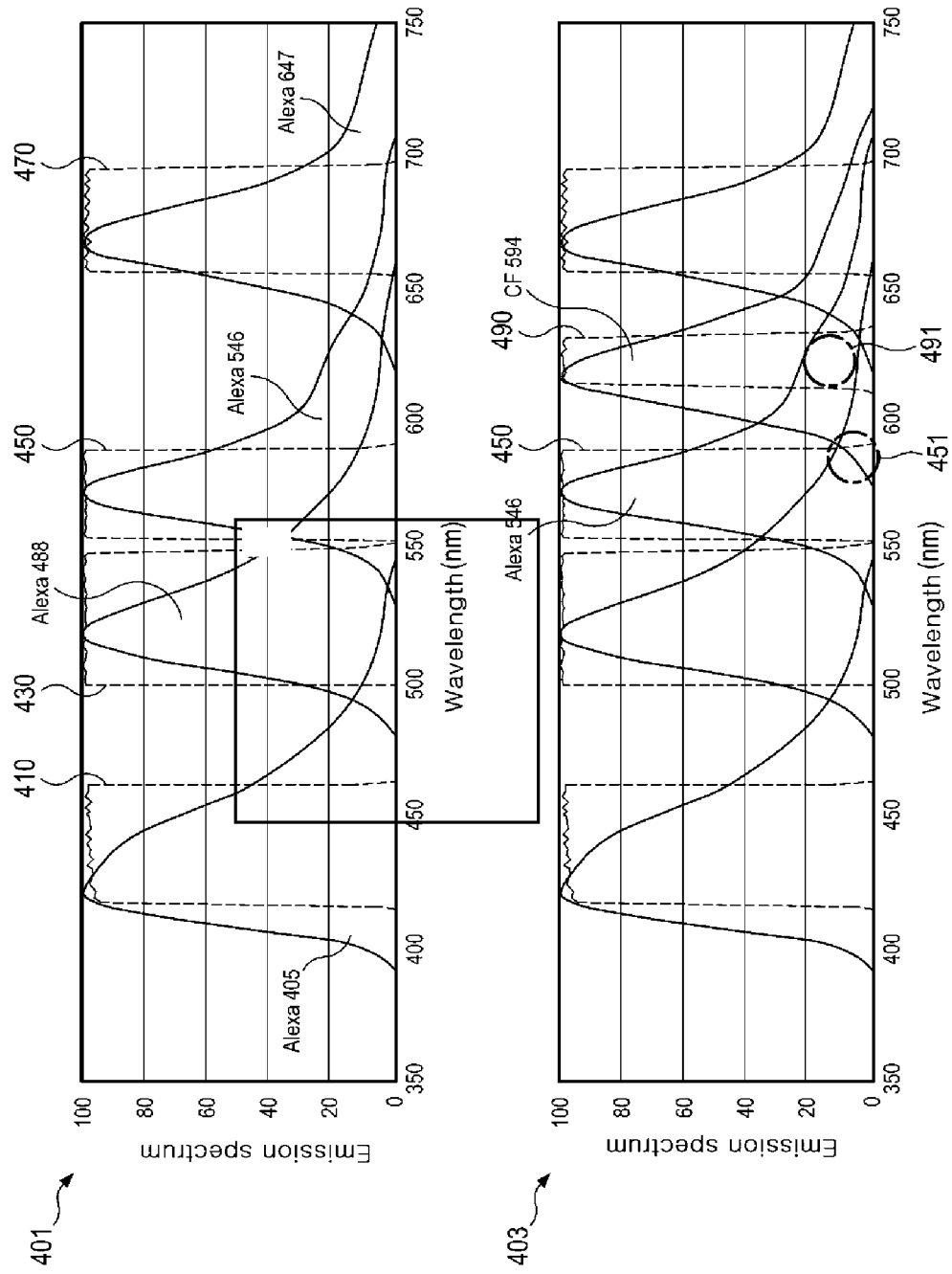
FIG. 4 is an exemplary diagram relating to features of a fluorescent material which is used to label a biomolecule in a conventional method of processing an image.

FIG. 4 is an exemplary diagram relating to features of a fluorescent material which is used to label a biomolecule in a conventional method of processing an image. In general, in order to observe several biomolecules in one biological sample, it is necessary to label biomolecules with different fluorescent materials and then individually obtain an image of each biomolecule. In the present disclosure, the biological sample may be simply denoted as a "sample." An image of each biomolecule included in a sample may be obtained by radiating, to a fluorescent material, light of a specific wavelength to which the fluorescent material responds, filtering the light emitted from a fluorescent material that is excited as a result through an emission filter, and photographing the light filtered through the emission filter, for example. In the present disclosure, the "emission filter" may be a filter that transmits light of a specific wavelength band.

A first graph 401 relating to the emission spectra of light that is emitted by a fluorescent material illustrates the emission spectra of a plurality of fluorescent materials (Alexa 405, Alexa 488, Alexa 546, Alexa 647).

The fluorescent material "Alexa 405" may be a fluorescent material that emits light of a wavelength between approximately 400 nm and 500 nm after absorbing light of a specific wavelength band. An image of a biomolecule labeled with the fluorescent material "Alexa 405" may be obtained by filtering light emitted from the fluorescent material "Alexa 405" through a first emission filter and photographing light of a wavelength band 410 that has been passed by the first emission filter. The wavelength band 410 passed by the first emission filter may be 470 nm or more to 520 nm or less, for example.

The fluorescent material "Alexa 488" may be a fluorescent material that emits light of a wavelength between approximately 500 nm and 600 nm after absorbing light of a specific wavelength band. In this case, an image of a biomolecule labeled with the fluorescent material "Alexa 488" may be obtained by filtering light emitted from the fluorescent material "Alexa 488" through a second emission filter and then photographing light of a wavelength band 430 that has been passed by the second emission filter. The wavelength band 430 passed by the second emission filter may be 500 nm or more to 560 nm or less, for example.

The fluorescent material "Alexa 546" may be a fluorescent material that emits light of a wavelength between approximately 550 nm and 650 nm after absorbing light of a specific wavelength band. In this case, an image of a biomolecule labeled with the fluorescent material "Alexa 546" may be obtained by filtering light emitted from the fluorescent material "Alexa 546" through a third emission filter and photographing light of a wavelength band 450 that has been passed by the third emission filter. The wavelength band 450 passed by the third emission filter may be 565 nm or more to 590 nm or less, for example.

The fluorescent material "Alexa 647" may be a fluorescent material that emits light of a wavelength between approximately 650 nm and 750 nm after absorbing light of a specific wavelength band. In this case, an image of a biomolecule labeled with the fluorescent material "Alexa 647" may be obtained by filtering light emitted from the fluorescent material "Alexa 647" through a fourth emission filter and photographing light of a wavelength band 470 that has been passed by the fourth emission filter. The wavelength band 470 passed by the fourth emission filter may be 660 nm or more to 740 nm or less, for example.

The wavelength bands of light that are absorbed in order for the respective fluorescent materials illustrated in the first graph 401 to be excited may be different. Furthermore, detailed numerical ranges of the emission spectra of the fluorescent materials described with reference to the first graph 401 are merely exemplary ranges for a description, and do not limit the present disclosure.

In an embodiment, it is assumed that a plurality of biomolecules is included in a sample and fluorescent materials (i.e., fluorescent materials combined with respective biomolecules) that label a plurality of biomolecules, respectively, identically respond to light having specific wavelengths (e.g., 350 nm or more to 400 nm or less). In this case, in order to obtain images of a plurality of biomolecules included in the sample, respectively, in general, emission spectra of the fluorescent materials for labeling the plurality of biomolecules, respectively, should not overlap or should rarely overlap. The reason for this is that if spectra of light emitted from different fluorescent materials overlap a lot, different biomolecules may be included in the same image.

For example, it is assumed that in a second graph 403 relating to emission spectra emitted by the fluorescent materials of FIG. 4, the fluorescent material "Alexa 546" emits light of a wavelength between approximately 550 nm and 650 nm and a fluorescent material "CF 594" emits light of a wavelength between approximately 575 nm and 700 nm. In such an assumption, emission spectra of the two fluorescent materials may include a section of 575 nm or more to 650 nm or less in common. In this case, if an image is photographed by using the third emission filter in order to obtain an image of a biomolecule labeled by the fluorescent material "Alexa 546", a biomolecule labeled by the fluorescent material "CF 594" may be at least partially included in the photographed image because the wavelength band 450 passed by the third emission filter is approximately 565 nm or more to 590 nm or less. Specifically, in a process of photographing, by the photographing device, an image of the biomolecule labeled by the fluorescent material "Alexa 546" by obtaining light having the wavelength band 450 passed by the third emission filter from the light emitted from the fluorescent material "Alexa 546", the photographing device may at least partially obtain a signal of the light emitted from the fluorescent material "CF 594." As a result, another biomolecule labeled by the fluorescent material "CF 594" may be at least partially included in the image of the biomolecule labeled by the fluorescent material "Alexa 546." Reference numeral 451 in FIG. 4 indicates a signal of another fluorescent material (e.g., "CF 594") that is obtained when the photographing device photographs the image of the biomolecule labeled by the fluorescent material "Alexa 546" by using the third emission filter. Furthermore, although an image is photographed by using a fifth emission filter that transmits light of a wavelength of about 610 nm or more to 630 nm or less in order to obtain the image of the biomolecule labeled by the fluorescent material "CF 594", the biomolecule labeled by the fluorescent material "Alexa 546" may be at least partially included in the photographed image. That is, in a process of photographing, by the photographing device, the image of the biomolecule labeled by the fluorescent material "CF 594" by obtaining the light having the wavelength band 490 passed by the fifth emission filter from the light emitted from the fluorescent material "CF 594", a signal of the light emitted from the fluorescent material "Alexa 546" may be at least partially obtained. As a result, another biomolecule labeled by the fluorescent material "Alexa 546" may be at least partially included in the image of the biomolecule labeled by the fluorescent material "CF 594." Reference numeral 491 in FIG. 4 indicates a signal of another fluorescent material (e.g., "Alexa 546") that is obtained when the photographing device photographs the image of the biomolecule labeled by the fluorescent material "CF 594" by using the fifth emission filter.

According to the aforementioned conventional technology, there are restrictions that emission spectra should not overlap as much as possible in order to observe a plurality of biomolecules included in a sample. Accordingly, there is a limit that only a maximum of four fluorescent materials can be simultaneously used.

Figure 5:
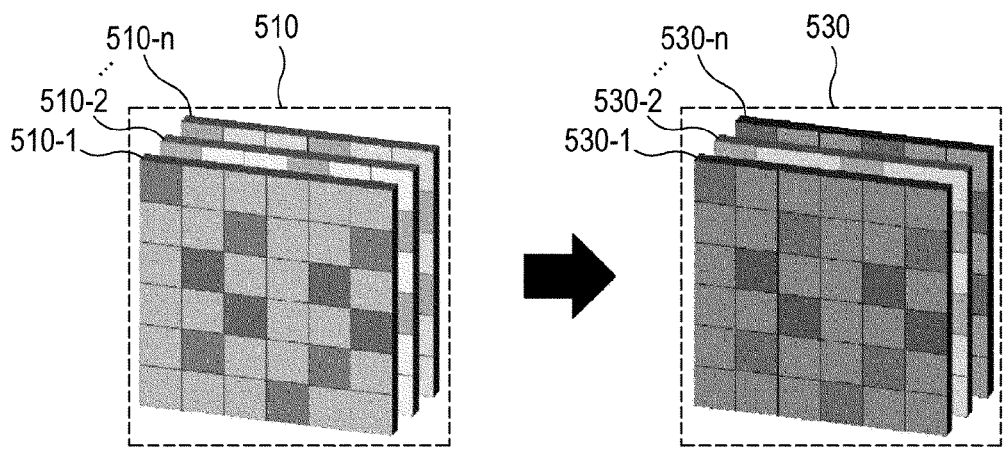
FIG. 5 is a concept view conceptually illustrating a process of generating a plurality of unmixed images from a plurality of mixed images according to an embodiment of the present disclosure.

FIG. 5 is a concept view conceptually illustrating a process of generating a plurality of unmixed images from a plurality of mixed images according to an embodiment of the present disclosure.

A mixed image 510 according to the present disclosure may include one or two or more mixed images. In some embodiments according to the present disclosure, if the mixed image 510 includes two or more mixed images, the mixed images may be divided and denoted as a first mixed image 510-1, a second mixed image 510-2 to an n-th mixed image 510-n (n is a natural number equal to or greater than 2), respectively.

The mixed image 510 may be an image that is obtained by labeling biomolecules included in a sample with fluorescent materials and then photographing, by the server 100, the sample. When the biomolecules included in the biological sample are labeled with the fluorescent materials (i.e., the fluorescent materials are combined with the biomolecules physically or chemically) and then light is radiated to the biological samble as described above, the fluorescent materials included in the biological sample are excited by absorbing light of a specific wavelength band, and then emit light of a specific wavelength band. At this time, the mixed image 510 of the biological sample may be obtained by photographing the light emitted by the fluorescent materials. The mixed image 510 is an image, that is, a target on which a method of processing an image according to the present disclosure is performed, and may be distinguished from an "unmixed image 530" that is generated by using the method of processing an image according to the present disclosure. That is, the mixed image 510 is an image on which the method of processing an image according to the present disclosure has not yet been performed, and may be an image in which another biomolecule (e.g., a biomolecule labeled with another fluorescent material having a similar emission spectrum or a biomolecule labeled in a previous staining round) is additionally included in addition to a target biomolecule. In the present disclosure, the term "mixed image" may be interchangeably used with an "input image."

The unmixed image 530 according to the present disclosure may include one or two or more unmixed images. In some embodiments according to the present disclosure, if the unmixed image 530 includes two or more unmixed images, the unmixed images may be divided and denoted as a first unmixed image 530-1, a second unmixed image 530-2 to an n-th unmixed image 530-n (n is a natural number equal to or greater than 2), respectively.

The unmixed image 530 may be an image that is obtained as a result of performing the method of processing an image according to the present disclosure on the mixed image 510. The unmixed image 530 may be an image of a targeted biomolecule. In the present disclosure, an "unmixed image of a specific biomolecule" may denote an image in which only a corresponding biomolecule is shown. For example, an unmixed image of a biomolecule "A" may be an image indicating a shape, a size, a form, or a color of the biomolecule "A" included in a sample. The unmixed image 530 may be generated to correspond to each biomolecule.

In various embodiments of the present disclosure, each of the plurality of mixed images 510-1, 510-2 to 510-n or the plurality of unmixed images 530-1, 530-2 to 530-n may be a single-channel image having one channel. The single channel image may mean an image having a single value (e.g., an integer of 0 or more to 255 or less) for each pixel. A pixel value of each pixel of a single-channel mixed image may be a value indicative of the intensity of light that is emitted from a fluorescent material when the photographing unit photographs the mixed image by obtaining light. A pixel value of each pixel of a single-channel unmixed image may be a value indicative of the intensity of light of each pixel in order to express an image of a specific biomolecule as a result of performing the method of processing an image according to the present disclosure. Furthermore, in the present disclosure, if it is expressed that the plurality of mixed images 510-1, 510-2 to 510-n or the plurality of unmixed images 530-1, 530-2 to 530-n is included in a multi-channel image, each channel of a multi-channel image may correspond to each of the plurality of mixed images 510-1, 510-2 to 510-n or the plurality of unmixed images 530-1, 530-2 to 530-n. For example, if a plurality of mixed images including three mixed images, that is, single channel images, is denoted as a "multi-channel mixed image", each channel of the corresponding multi-channel mixed image may correspond to each mixed image included in the plurality of mixed images. Furthermore, according to the present disclosure, if a plurality of mixed images or a plurality of unmixed images that are individually obtained is indicated as a multi-channel mixed image or a multi-channel unmixed image by corresponding each of the plurality of mixed images or each of the plurality of unmixed images to one channel, the plurality of mixed images or the plurality of unmixed images may be simultaneously indicated on one multi-channel image. For example, if three mixed images are indicated as an RGB image having three channels by corresponding the three mixed images to a red channel, a green channel, and a blue channel, respectively, the three mixed images may be simultaneously indicated on the RGB image.

In the method of processing an image according to the present disclosure, the unmixed image 530 may be generated from the mixed image 510.

In an embodiment, the server 100 may generate the plurality of unmixed images 530-1, 530-2 to 530-*n* by unmixing the plurality of mixed images 510-1, 510-2 to 510-*n* based on at least one parameter for unmixing the plurality of mixed images 510-1, 510-2 to 510-*n*. Assuming that a plurality of mixed images includes two mixed images for a description, two unmixed images generated from the plurality of mixed images based on at least one parameter may be represented like Equation 1.

$$X_1 = Y_1 + \theta_{12} Y_2 \quad \text{[Equation 1]}$$
$$X_2 = \theta_{21} Y_1 + Y_2$$

In Equation 1, $Y_1$ and $Y_2$ indicate the mixed images, $\theta_{12}$ and $\theta_{21}$ indicate parameters necessary to generate the unmixed images, and $X_1$ and $X_2$ indicate the unmixed images. In this case, $\theta_{12}$ and $\theta_{21}$ may be parameters for determining the weight (or the contribution ratio) of each mixed image. The processor 110 may generate the unmixed images by weighted-summing (or linear overlap) the mixed images based on at least one parameter $\theta_{12}$ or $\theta_{21}$. For example, according to Equation 1, the unmixed image $X_1$ may be generated as a result of linearly overlapping $Y_1$ of one multiple and $Y_2$ of $\theta_{12}$ multiple. The unmixed image $X_2$ may be generated as a result of linearly overlapping $Y_1$ of $\theta_{21}$ multiple and $Y_2$ of one multiple.

In the present disclosure, an "operation of unmixing a plurality of mixed images based on at least one parameter" may also be represented based on a matrix. In the present disclosure, such a matrix may be denoted as an "unmixing matrix", and may include at least one element for generating a plurality of unmixed images of respective biomolecules from a plurality of mixed images. That is, the unmixing matrix may include at least one element that determines a linear overlap ratio between the plurality of mixed images. If Equation 1 is expressed based on a matrix, this may be exemplified like Equation 2.

$$\begin{bmatrix} X_1 \\ X_2 \end{bmatrix} = \begin{bmatrix} 1 & \theta_{12} \\ \theta_{21} & 1 \end{bmatrix} \begin{bmatrix} Y_1 \\ Y_2 \end{bmatrix} \quad \text{[Equation 2]}$$

In an embodiment, the server 100 may generate the plurality of unmixed images 530-1, 530-2 to 530-*n* by subtracting a predetermined constant (also called a "constant offset") from each of the plurality of mixed images 510-1, 510-2 to 510-*n* and then weighted-summing a plurality of mixed images from each of which a value of a pixel has been subtracted by the predetermined constant.

$$\begin{bmatrix} X_1 \\ X_2 \end{bmatrix} = \begin{bmatrix} 1 & \theta_{12} \\ \theta_{21} & 1 \end{bmatrix} \begin{bmatrix} y_1 - \Theta_{b1} \\ y_2 - \Theta_{b2} \end{bmatrix} \quad \text{[Equation 3]}$$

In Equation 3, $\Theta_{b1}$ and $\Theta_{b2}$ indicate constant offsets for the mixed images $Y_1$ and $Y_2$, respectively. The server 100 may generate each unmixed image based on a result of the weighted sum of $(Y_1 - \Theta_{b1})$ and $(Y_2 - \Theta_{b2})$ after subtracting the constant offset from each pixel value included in the mixed image.

In Equation 1 to 3, it has been assumed that a plurality of mixed images includes two mixed images, but this does not limit the present disclosure. A plurality of mixed images may include three or more mixed images.

Figure 6:
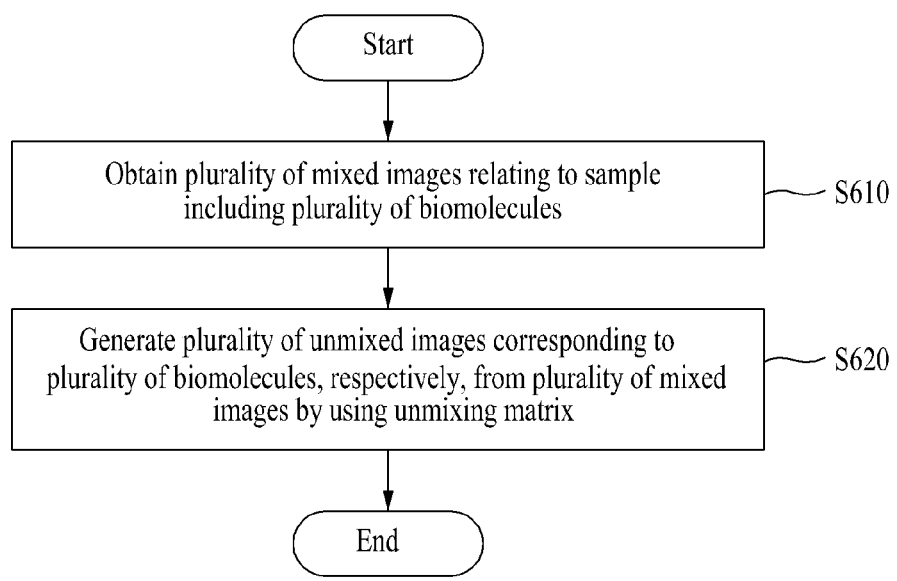
FIG. 6 is a flowchart illustrating an operation of the server generating an unmixed image of each of a plurality of biomolecules from a plurality of mixed images relating to a sample by using an unmixing matrix according to an embodiment of the present disclosure.

FIG. 6 is a flowchart illustrating an operation of the server 100 generating an unmixed image of each of a plurality of biomolecules from a plurality of mixed images of a sample by using an unmixing matrix according to an embodiment of the present disclosure.

The server 100 may obtain a plurality of mixed images of a sample including a plurality of biomolecules (S610). Specifically, the processor 110 may obtain the plurality of mixed images based on an operation of inputting, by a user of the server 100, the plurality of mixed images through the input unit 140. Furthermore, the processor 110 may obtain the plurality of mixed images by photographing an image of a sample through a photographing unit (not illustrated) of the server 100. Furthermore, the processor 110 may obtain the plurality of mixed images from an external device or the user terminal 200 through the communication interface 120. The plurality of mixed images (or input images) may be represented as a matrix like Equation 4, for example.

$$Y = \begin{bmatrix} (\text{First input img})_1 & \cdots & (\text{First input img})_m \\ \vdots & \vdots & \vdots \\ (n^{th} \text{ input img})_1 & \cdots & (n^{th} \text{ input img})_m \end{bmatrix} \quad \text{[Equation 4]}$$

In Equation 4, Y indicates a matrix relating to the plurality of mixed images (i.e., the plurality of input images). The plurality of input images may be a plurality of mixed images obtained as a result of staining a sample n times in a process of staining the sample and photographing the sample. In Equation 4, ($i^{th}$ input img)$_j$ indicates a value of a j-th pixel of an i-th input image. In Equation 4, the size of a row in the matrix may be the same size as the number of plurality of input images. For example, if the number of plurality of input image is n, the size of a row in the matrix Y may be n. In Equation 4, the size of a column in the matrix may be the same size as the number of pixels included in each input image. For example, if an input image is a two-dimensional (2-D) image and has resolution of 1024 (i.e., the number of pixels in a transverse direction)×1024 (i.e., the number of pixels in a longitudinal direction) and thus the number of pixels included in the input image may be 1048576 (=1024*1024), the size of the column in the matrix Y may be 1048576. That is, if the size of the column in the matrix Y is n and the size of a row in the matrix is m (i.e., an n×m matrix), the matrix Y may be interpreted as a matrix relating to n input images each including m pixels.

Next, the server 100 may generate a plurality of unmixed images corresponding to a plurality of biomolecules, respectively, from the plurality of mixed images by using an unmixing matrix (S620). The unmixing matrix according to the present disclosure is a rectangle matrix, and may be a square matrix in which the sizes of a row and a column are the same or may be a rectangle matrix in which the sizes of a row and a column are different from each other. The unmixing matrix may be represented like Equation 5, for example.

$$U = \begin{bmatrix} \alpha_{11} & \cdots & \alpha_{1n} \\ \vdots & \ddots & \vdots \\ \alpha_{k1} & \cdots & \alpha_{kn} \end{bmatrix} \quad \text{[Equation 5]}$$

In Equation 5, $\alpha_{ij}$ indicates a value of an i-row j-column element (or parameter) in the unmixing matrix. The size of a column in the unmixing matrix U may be the same size as the number of mixed images, that is, a target of a matrix operation. For example, the size of a column in an unmixing matrix for n mixed images may be n as in the number of mixed images. The size of a row (i.e., k) in the unmixing matrix U may be the same as or different from the size of the column (n) in the unmixing matrix U. The size (i.e., k) of the row in the unmixing matrix U may be smaller than or equal to the size of the column (n) in the unmixing matrix U.

The processor 110 may generate the plurality of unmixed images by processing the plurality of mixed images by using the unmixing matrix. The mixed image according to Equation 4 and the plurality of unmixed images generated based on the unmixing matrix according to Equation 5 may be represented like Equation 6.

$$X = U \cdot Y = \begin{bmatrix} (\text{First unmixed img})_1 & \cdots & (\text{First unmixed img})_m \\ \vdots & \vdots & \vdots \\ (n^{th} \text{ unmixed img})_1 & \cdots & (n^{th} \text{ unmixed img})_m \end{bmatrix} \quad [\text{Equation 6}]$$

In Equation 6, X indicates a matrix that is obtained as a result of matrix multiplication for the unmixing matrix U and the matrix Y for the plurality of mixed images. The size of a row in the matrix X for the plurality of unmixed images may be indicated as the number of generated unmixed images. The size of a column in the matrix X for the plurality of unmixed images may be indicated as the number of pixels included in each unmixed image. Each unmixed image may be an image of a corresponding specific biomolecule. In Equation 6, $(i^{th}$ unmixed img$)_j$ indicates a value of a j-th pixel of an i-th unmixed image. For example, a first unmixed image may indicate an image of a biomolecule "A" included in a sample. An $n^{th}$ unmixed image may indicate an image of a biomolecule "B" included in the sample.

As described above, the processor 110 may generate the plurality of unmixed images corresponding to a plurality of biomolecules, respectively, by obtaining the plurality of mixed images and performing a matrix operation on the plurality of mixed images by using the unmixing matrix.

In an embodiment, the unmixing matrix may be a square matrix in which the sizes of a row and a column are the same. For example, the unmixing matrix, that is, a square matrix, may be represented like Equation 7.

$$U = \begin{bmatrix} \alpha_{11} & \cdots & \alpha_{1n} \\ \vdots & \ddots & \vdots \\ \alpha_{n1} & \cdots & \alpha_{nn} \end{bmatrix} \quad [\text{Equation 7}]$$

In Equation 7, an unmixing matrix U may be a square matrix in which the sizes of a row and a column are the same n (n is a natural number equal to or greater than 1). The processor 110 may obtain n unmixed images by performing a matrix operation on n mixed images based on such the unmixing matrix U.

Hereinafter, a method of determining a histogram or a probability distribution function from a multi-channel image is described with reference to FIGS. 7 to 10.

Figure 7:
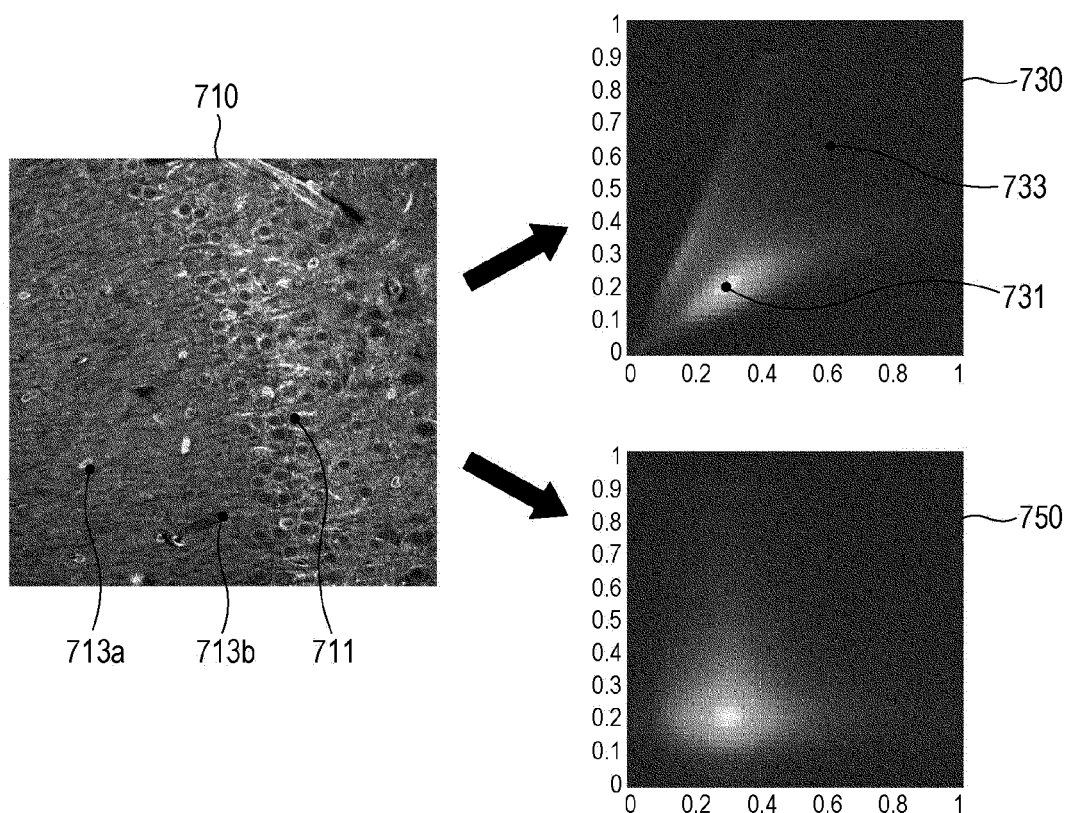
FIG. 7 is an exemplary diagram illustrating histograms that are determined based on a multi-channel image by using different methods according to an embodiment of the present disclosure.

FIG. 7 is an exemplary diagram illustrating histograms that are determined based on a multi-channel image by using different methods according to an embodiment of the present disclosure. A first image 710 may be a multi-channel image including a plurality of mixed images, for example. The channels of the first image 710 may correspond to the plurality of mixed images, respectively. Hereinafter, in the present disclosure, the first image 710 is described as a multi-channel image including two channels, but this is an assumption for convenience of description, and does not limit the present disclosure. For example, a first image included in the first image 710 (or a first channel of the first image) may be an image (or channel) obtained by staining a biomolecule "A1" included in a sample with a fluorescent material "A2" and photographing light emitted from the fluorescent material "A2." Furthermore, for example, a second image included in the first image 710 (or a second channel of the first image) may be an image (or channel) obtained by staining a biomolecule "B1" included in the sample with a fluorescent material "B2" and photographing light emitted from the fluorescent material "B2" or may be an image (or channel) obtained by staining the biomolecules "A1" and "B1" included in the sample with the fluorescent material "A2" and "B2", respectively, and photographing light emitted from the fluorescent material "A2" and the fluorescent material "B2."

The processor 110 may determine two or more histograms by using different methods based on a multi-channel image including a plurality of single-channel images. For example, the processor 110 may determine one histogram based on values of pixels at the same location within a plurality of single-channel images, and may determine another histogram based on values of pixels at different locations within the plurality of single-channel images. For example, as illustrated in FIG. 7, a (1-1)-th histogram 730 or a (1-2)-th histogram 750 may be a histogram determined by using a different method in relation to the first image 710. In an embodiment, the (1-1)-th histogram 730 may be a histogram determined based on values of pixels at the same location within a plurality of mixed images included in the first image 710. The (1-2)-th histogram 750 may be a histogram determined based on values of pixels at different locations within a plurality of mixed images included in the first image 710. Hereinafter, some methods of determining a histogram according to the present disclosure are described in detail with reference to FIGS. 8 and 9.

Figure 8:
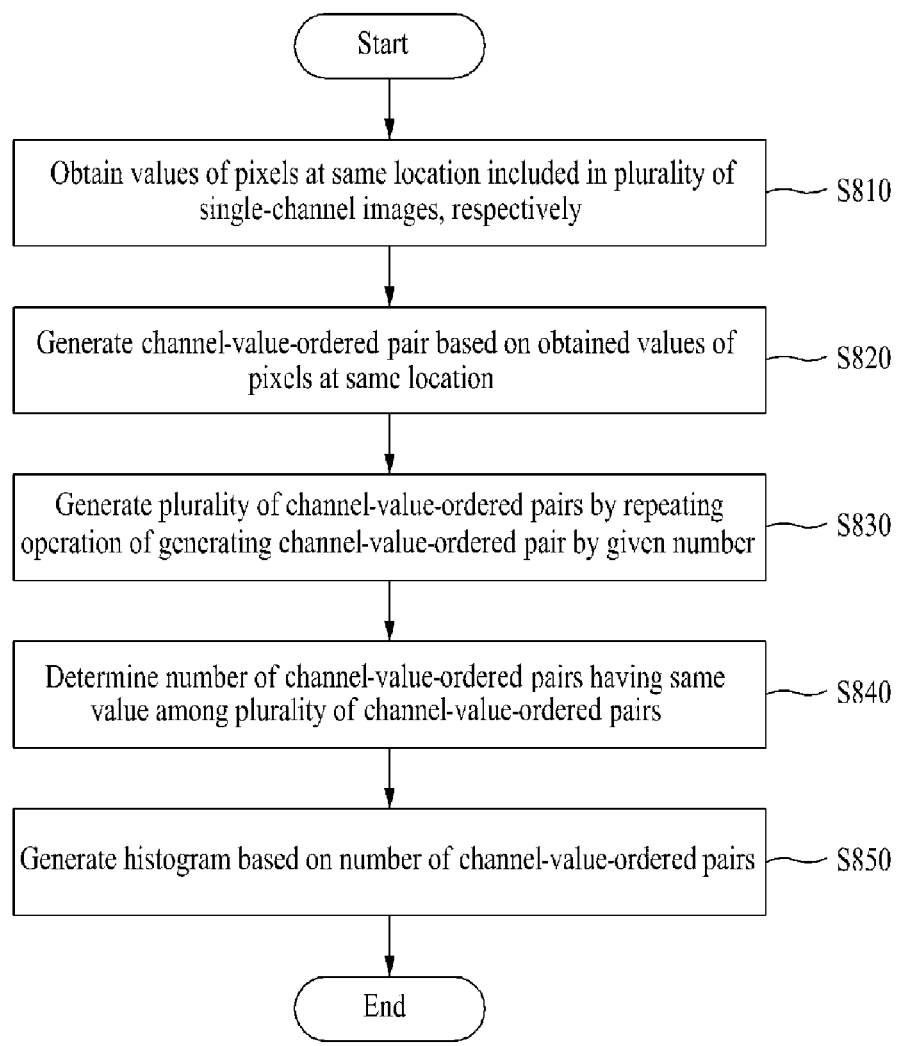
FIG. 8 is a flowchart illustrating an operation of the server determining a histogram based on values of pixels at the same location, which are included in a plurality of single-channel images, according to an embodiment of the present disclosure.

FIG. 8 is a flowchart illustrating an operation of the server 100 determining a histogram based on values of pixels at the same location, which are included in a plurality of single-channel images, according to an embodiment of the present disclosure. In FIG. 8, the first image 710 of FIG. 7 is described as an example of a multi-channel image including a plurality of single-channel images.

The processor 110 may obtain values of pixels at the same location included in a plurality of single-channel images, respectively (S810). For example, the processor 110 may obtain a pixel value (e.g., 0.9) from a first location 711 within the first image included in the first image 710 (or a first channel of the first image). Furthermore, the processor 110 may obtain a pixel value (e.g., 0.8) from the first location 711 within the second image included in the first image 710 (or a second channel of the first image). As described above, the processor 110 may obtain pixel values of pixels at the same location (i.e., a first location) included in a plurality of mixed images included in the first image 710, respectively.

Next, the processor 110 may generate a channel-value-ordered pair based on the values of the pixels at the same location obtained from the plurality of single-channel images, respectively (S820). The channel-value-ordered pair may include a plurality of elements. For example, a channel-value-ordered pair for the first image 710 may include two elements. The channel-value-ordered pair for the first image 710 may be represented like (v1, v2), for example. In this case, a first element v1 included in the channel-value-ordered pair (v1, v2) may be a value of a pixel included in a first channel of the first image 710, and a second element (i.e., v2) included therein may be a value of a pixel included in a second channel of the first image 710. The value of each element included in the channel-value-ordered pair is a value that means the intensity of light, and may be a real number included in a given range (e.g., 0 or more to 1 or less). If a pixel value obtained from the first location 711 within the first channel of the first image 710 is 0.9 and a pixel value obtained from the first location 711 within the second channel of the first image 710 is 0.8, the processor 110 may generate a channel-value-ordered pair having a value of (0.9, 0.8).

Next, the processor 110 may generate a plurality of channel-value-ordered pairs by repeating an operation of generating the channel-value-ordered pair a specific number of times (S830). For example, the processor 110 may generate channel-value-ordered pairs by sequentially repeating step S810 and S820 a specific number of times.

Next, the processor 110 may determine the number of channel-value-ordered pairs having the same value among the plurality of channel-value-ordered pairs (S840). For example, it is assumed that generated channel-value-ordered pairs are [(0.9, 0.8), (0.8, 0.2), (0.6, 0.0), (0.9, 0.8), (0.9, 0.8), (0.9, 0.8), (0.8, 0.2), (0.6, 0.0), (0.8, 0.2), (0.6, 0.0)]. In this case, the processor 110 may determine the number of channel-value-ordered pairs having the same value, like four ordered pairs (0.9, 0.8), three ordered pairs (0.8, 0.2), and three ordered pairs (0.6, 0.0).

Next, the processor 110 may generate a histogram based on the number of channel-value-ordered pairs (S850). In an embodiment, the histogram may be represented on a 2-D coordinate axis. That is, the histogram may include a transverse axis (x axis) corresponding to a first element of a channel-value-ordered pair and a longitudinal axis (y axis) corresponding to a second element of the channel-value-ordered pair. A pixel corresponding to each channel-value-ordered pair in the histogram may be represented to have a different color or different brightness based on the number of the corresponding channel-value-ordered pairs. For example, a pixel corresponding to each channel-value-ordered pair in a histogram may be represented to be brighter as the number of corresponding channel-value-ordered pairs is increased or may be represented to be closer to a second color (e.g., red) from a first color (e.g., blue). This is described with reference to FIG. 7. The (1-1)-th histogram 730 may be a histogram generated as a result of performing, by the processor 110, step S810 to S850 on the first image 710. Furthermore, a pixel indicated by reference numeral 731 is a pixel that has 0.3 as an x value and 0.2 as a y value in the (1-1)-th histogram 730, and may be a pixel corresponding to a channel-value-ordered pair (0.3, 0.2). A pixel indicated by reference numeral 733 is a pixel that has 0.6 as an x value and has 0.6 as a y value in the (1-1)-th histogram 730, and may be a pixel corresponding to a channel-value-ordered pair (0.6, 0.6). If it is assumed that the number of channel-value-ordered pairs having the value of (0.3, 0.2) among channel-value-ordered pairs generated from the first image 710 is greater than the number of channel-value-ordered pairs having the value of (0.6, 0.6), the pixel 731 corresponding to the channel-value-ordered pair (0.3, 0.2) in the (1-1)-th histogram 730 may be represented to be a brighter color than a pixel 733 corresponding to the channel-value-ordered pair (0.6, 0.6).

In another embodiment, a histogram may be represented on a 3-D coordinate axis. In this case, the histogram may include a first axis (x axis) corresponding to a first element of a channel-value-ordered pair, a second axis (y axis) corresponding to a second element of the channel-value-ordered pair, and a third axis (z axis) corresponding to the number of channel-value-ordered pairs.

After performing step S850, the processor 110 may additionally perform an operation of determining a probability distribution function based on the histogram. Hereinafter, in the present disclosure, the "probability distribution function" may be denoted as a term called as "probability distribution." For example, the processor 110 may approximately determine a probability distribution by normalizing the histogram generated as a result of the execution of step S850. This is described with reference to FIG. 7. A probability distribution determined based on the (1-1)-th histogram 730 may be a consecutive probability distribution function having a data distribution similar to that of the (1-1)-th histogram 730.

Figure 9:
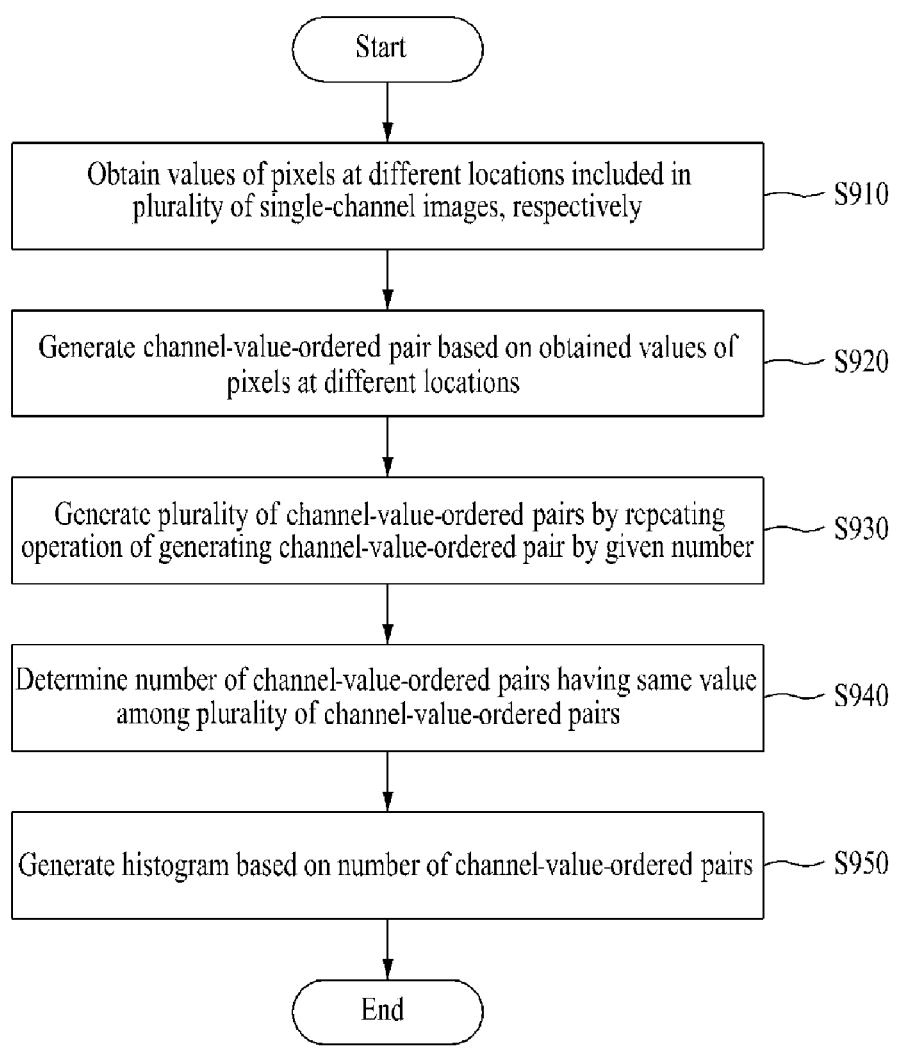
FIG. 9 is a flowchart illustrating an operation of the server determining a histogram based on values of pixels at different locations, which are included in each of a plurality of single-channel images, according to an embodiment of the present disclosure.

FIG. 9 is a flowchart illustrating an operation of the server 100 determining a histogram based on values of pixels at different locations, which are included in each of a plurality of single-channel images, according to an embodiment of the present disclosure. In FIG. 9, the first image 710 of FIG. 7 is described as an example of a multi-channel image including a plurality of single-channel images.

The processor 110 may obtain values of pixels at different locations included in a plurality of single-channel images, respectively (S910). For example, the processor 110 may obtain a pixel value (e.g., 0.5) from a (2-1)-th location 713a within the first image included in the first image 710 (or a first channel of the first image). Furthermore, the processor 110 may obtain a pixel value (e.g., 0.1) from a (2-2)-th location 713b within the first image included in the first image 710 (or the first channel of the first image). The (2-1)-th location 713a and the (2-2)-th location 713b may be locations having different coordinate values. As described above, the processor 110 may obtain pixel values of pixels at different locations included in a plurality of mixed images included in the first image 710, respectively.

Next, the processor 110 may generate a channel-value-ordered pair based on the values of pixels at different locations, which have been obtained from the plurality of single-channel images, respectively (S920). For example, if the value of the pixel obtained from the (2-1)-th location 713a within the first channel of the first image 710 is 0.5 and the value of the pixel obtained from the (2-2)-th location 713b within the second channel of the first image 710 is 0.1, the processor 110 may generate a channel-value-ordered pair having a value of (0.5, 0.1).

Next, the processor 110 may generate a plurality of channel-value-ordered pairs by repeating the operation (i.e., S910 and S920) of generating the channel-value-ordered pair by a given number (S930), may determine the number of channel-value-ordered pairs having the same value among the plurality of channel-value-ordered pairs (S940), and may generate a histogram based on the number of channel-value-ordered pairs (S950). Steps S930 to S950 may be performed identically with or similar to steps S830 to S850 by the processor 110, and thus a description of redundant contents is omitted. The (1-2)-th histogram 750 of FIG. 7 may be a histogram that is generated as a result of performing, by the processor 110, steps S910 to S950 on the first image 710.

After performing step S950, the processor 110 may additionally perform an operation of determining a probability distribution function based on the generated histogram. For example, the processor 110 may approximately determine a probability distribution by normalizing the histogram generated as a result of performing step S950. This is described with reference to FIG. 7. The probability distribution determined based on the (1-2)-th histogram 750 may be a consecutive probability distribution function having a data distribution similar to that of the (1-2)-th histogram 750.

The server 100 according to the present disclosure may determine histograms or probability distributions for a corresponding image by using a different method based on a multi-channel image including a plurality of single-channel images, as described above with reference to FIGS. 8 and 9.

In the present disclosure, a term "dependency" or "similarity" between a plurality of images is a term indicating how much information included in a plurality of images is associated with each other, and may be used as a meaning that is contrasted with probabilistic independency. If a plurality of images has high dependency, pixels corresponding to the same location in respective images may have a specific tendency between pixel values. For example, if a pixel value of the first channel among pixel values corresponding to the same location in respective images is low, a pixel value of the second channel may be high with a high probability. On the contrary, if the pixel value of the first channel is high, the pixel value of the second channel may be high with a high probability. In contrast, if a plurality of images has low dependency, specific tendency may not be present between pixel values of those pixels although the pixels correspond to the same location in respective images. In the present disclosure, if "specific tendency is not present" between a plurality of pixel values, this may mean that the plurality of pixel values does not affect each other and an intensity relation relating to the intensities of the plurality of pixel values is randomly determined. Furthermore, in the present disclosure, the term "independency" may be used as a term indicating how much information included in a plurality of images is independent to each other. That is, dependency and independency are opposite concepts. It may be represented that the higher dependency between a plurality of images, the smaller independency is and the lower dependency between a plurality of images, the greater independency is. A plurality of mixed images according to the present disclosure may have high dependency. Furthermore, a plurality of unmixed images generated from a plurality of mixed images may have low dependency.

Referring back to FIG. 7, the first image 710 may be a multi-channel image, where each of the plurality of channels corresponds to one mixed image included in a plurality of mixed images, respectively. As described above, the plurality of mixed images may have high dependency. Pixels at the same location included in mixed images, respectively, may have pixel values having the same or similar intensity. Accordingly, if a histogram is determined based on values of pixels at the same location included in a plurality of mixed images, respectively, the value of a first element and the value of a second element included in a channel-value-ordered pair may be generally the same or similar to each other. For example, as in the (1-1)-th histogram 730 generated based on values of pixels at the same location included in a plurality of mixed images, respectively, a specific correlation may appear between a value of the first element and a value of the second element.

In the present disclosure, a histogram generated based on values of pixels at the same location included in a plurality of single-channel images, respectively, may be denoted as a "joint histogram" for the images. Furthermore, a probability distribution function determined based on the joint histogram may be denoted as a "joint probability distribution." For example, the (1-1)-th histogram 730 may be a joint histogram for a plurality of mixed images included in the first image 710.

If a histogram is generated based on values of pixels at different locations within a plurality of mixed images included in the first image 710, specific tendency may not be present between the value of a first element and the value of a second element which are included in a channel-value-ordered pair. For example, as in the (1-2)-th histogram 750 generated based on values of pixels at different locations included in a plurality of mixed images, respectively, a specific correlation may not appear between a value of a first element and a value of a second element, which are included in a channel-value-ordered pair.

In the present disclosure, a histogram generated based on values of pixels at different locations included in a plurality of single-channel images, respectively, may be indicated as a "marginal histogram" for the images. Furthermore, a probability distribution function determined based on the marginal histogram may be denoted as a "marginal probability distribution." For example, the (1-2)-th histogram 750 may be a marginal histogram for a plurality of mixed images included in the first image 710.

Hereinafter, two or more histograms determined based on a multi-channel image are described with reference to FIG. 10. If a plurality of channels included in the multi-channel image are unmixed images, respectively, the two or more histograms are determined based on the multi-channel image.

Figure 10:
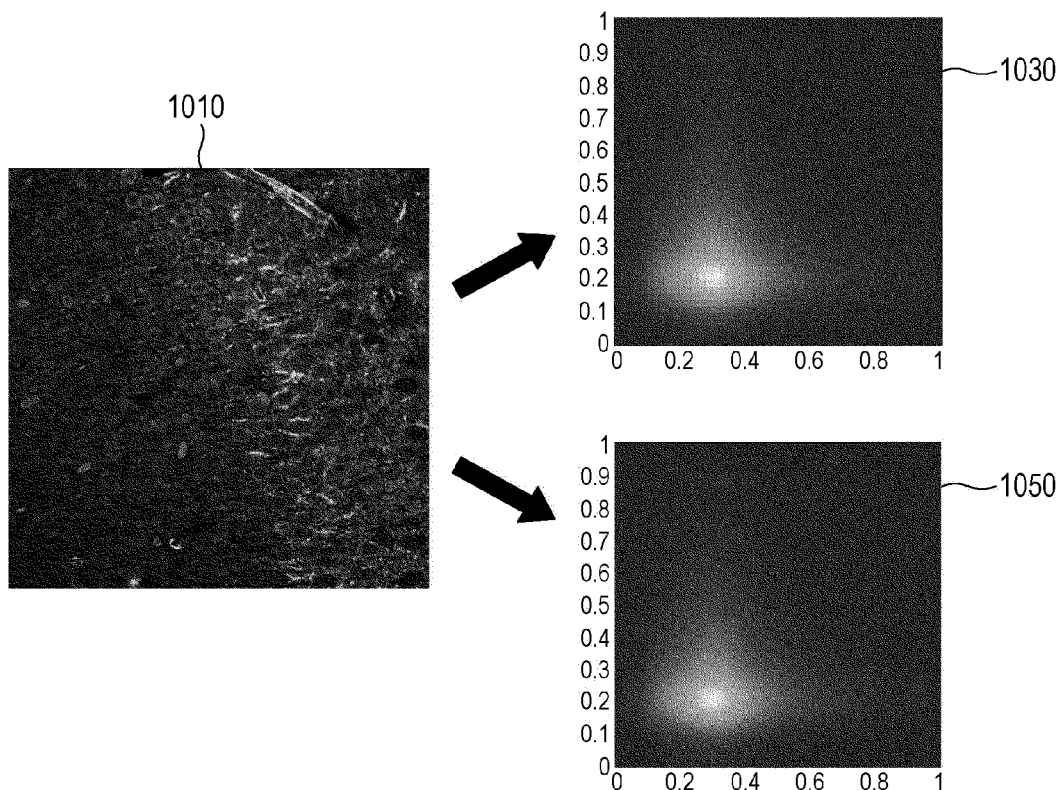
FIG. 10 is an exemplary diagram illustrating histograms that are determined based on a multi-channel image by using different methods according to another embodiment of the present disclosure.

FIG. 10 is an exemplary diagram illustrating histograms that are determined based on a multi-channel image by using different methods according to another embodiment of the present disclosure. A second image 1010 may be a multi-channel image including a plurality of unmixed images, for example. The second image 1010 may be a multi-channel image including a plurality of unmixed images generated as a result of processing, by the processor 110, a plurality of mixed images by using an unmixing matrix. Hereinafter, in the present disclosure, the second image 1010 is described as a multi-channel image having two channels, but this is merely an assumption for convenience of description and does not limit the present disclosure. For example, a first image included in the second image 1010 (or a first channel of the second image) may be an image of a biomolecule "A1" included in a sample. Furthermore, for example, a second image included in the second image 1010 (or a second channel of the second image) may be an image of a biomolecule "B1" included in the sample.

A (2-1)-th histogram 1030 and a (2-2)-th histogram 1050 may be histograms determined in relation to the second image 1010 by using methods similar to those of the (1-1)-th histogram 730 and the (1-2)-th histogram 750 described with reference to FIG. 7. For example, the (2-1)-th histogram 1030 may be a joint histogram determined based on values of pixels at the same location within a plurality of single-channel images included in the second image 1010. The (2-2)-th histogram 1050 may be a marginal histogram determined based on values of pixels at different locations within a plurality of single-channel images included in the second image 1010. Specific tendency may not be present between pixel values of pixels corresponding to the same location in a plurality of unmixed images. That is, a specific correlation may not appear in histograms determined with respect to a plurality of unmixed images having low dependency. For example, if the (2-1)-th histogram 1030 and the (2-2)-th histogram 1050 are generated with respect to the second image 1010 including a plurality of unmixed images, specific tendency may not be present between the value of a first element and the value of a second element which are included in a channel-value-ordered pair in both the histograms.

Figure 11:
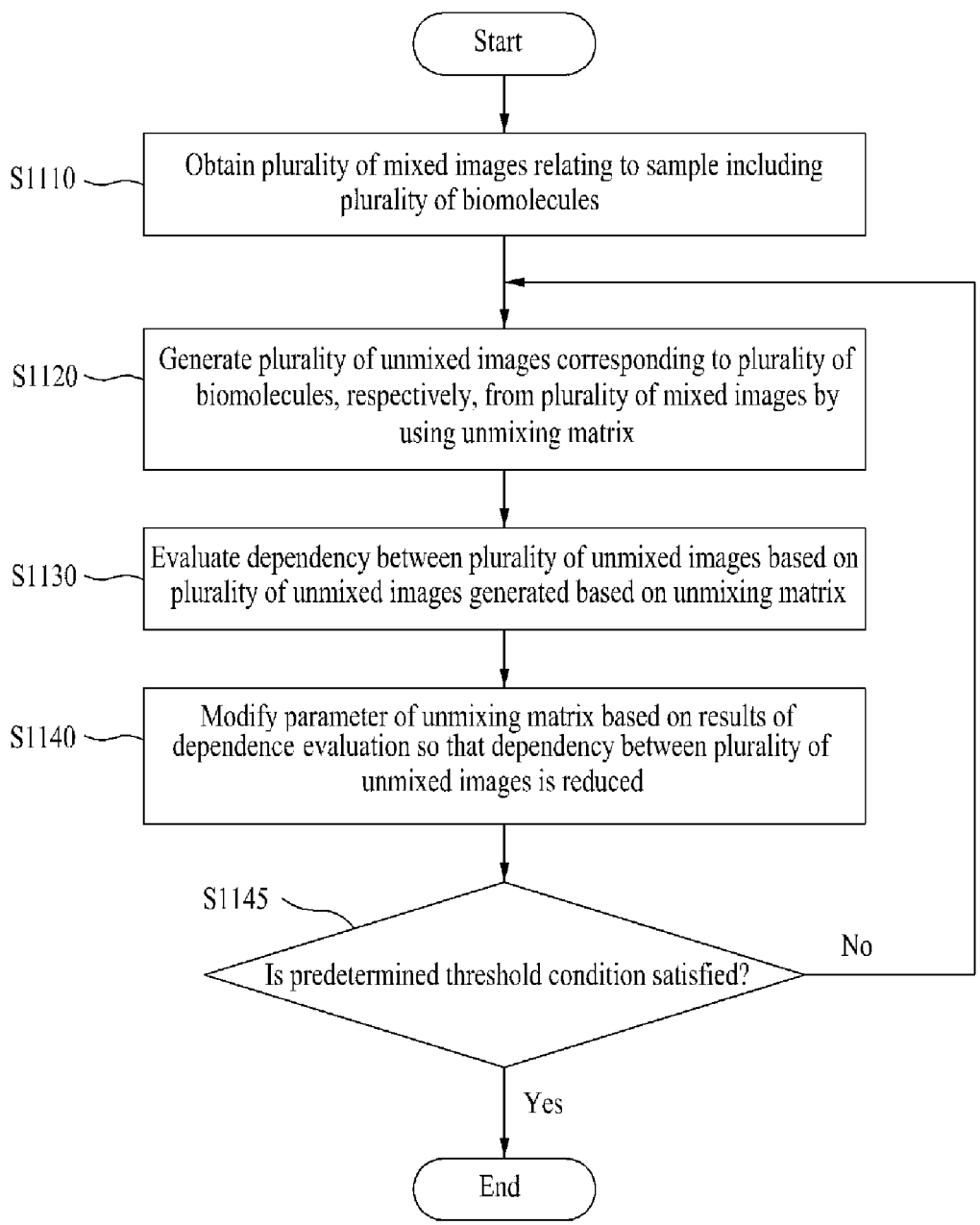
FIG. 11 is a flowchart illustrating an operation of the server updating a parameter of an unmixing matrix according to an embodiment of the present disclosure.

FIG. 11 is a flowchart illustrating an operation of the server 100 updating a parameter of an unmixing matrix according to an embodiment of the present disclosure.

The processor 110 may obtain a plurality of mixed images relating to a sample including a plurality of biomolecules (S1110). The processor 110 may generate a plurality of unmixed images corresponding to the plurality of biomolecules, respectively, from the plurality of mixed images by using an unmixing matrix (S1120). Step S1110 or S1120 may be performed by the processor 110 identically with or similar to step S610 or S620 described with reference to FIG. 6.

Next, the processor 110 may evaluate dependency between the plurality of unmixed images based on the plurality of unmixed images generated based on the unmixing matrix (S1130). The dependency between the plurality of unmixed images may be evaluated based on a specific algorithm that is performed by the processor 110 or may be evaluated by performing, by the processor 110, a given operation by using an artificial neural network model. Furthermore, the processor 110 may modify a parameter of the unmixing matrix based on the results of the dependence evaluation so that the dependency between the plurality of unmixed images is reduced (S1140).

According to various embodiments of the present disclosure, the processor 110 may evaluate dependency between the plurality of unmixed images based on histograms generated with respect to the plurality of unmixed images. Specifically, the processor 110 may calculate a value indicative of dependency between the plurality of unmixed images (hereinafter also referred to as a "dependence evaluation value") according to a predetermined algorithm (or an equation) based on histograms generated with respect to the plurality of unmixed images.

In a first embodiment in which the dependency between the plurality of unmixed images is evaluated based on the histograms generated with respect to the plurality of unmixed images, the processor 110 may evaluate the dependency by calculating mutual information between the plurality of unmixed images. The "mutual information" is a value derived from an information theory. Mutual information between two variables may indicate the total amount of information shared between the two variables. For example, mutual information between two random variables may be 0. The processor 110 may calculate the mutual information based on a joint histogram or marginal histogram which may be generated based on the plurality of unmixed images. Mutual information between two unmixed images may be represented like Equation 8, for example.

$$I(X_1; X_2) = \sum_{x_2} \sum_{x_1} p_{(X_1, X_2)}(x_1, x_2) \log\left(\frac{p_{(X_1, X_2)}(x_1, x_2)}{p_{X_1}(x_1) p_{X_2}(x_2)}\right) \quad \text{[Equation 8]}$$

In Equation 8, $X_1$ and $X_2$ indicate different unmixed images. $I(X_1; X_2)$ indicates calculated mutual information between two unmixed images. In Equation 8, $p_{(X_1, X_2)}(x_1, x_2)$ on the right side indicates a joint histogram or a joint probability distribution that is determined based on values of pixels at the same location, which are included in the two unmixed images $X_1$ and $X_2$, respectively. The joint histogram or the joint probability distribution for the two unmixed images $X_1$ and $X_2$ may be generated as a result of performing, by the processor 110, each step of FIG. 8 on the two unmixed images $X_1$ and $X_2$, for example. In Equation 8, $p_{X_1}(x_1) p_{X_2}(x_2)$ on the right side indicates a marginal histogram or a marginal probability distribution that is determined based on values of pixels at different locations, which are included in the two unmixed images $X_1$ and $X_2$, respectively. The marginal histogram or the marginal probability distribution for the two unmixed images $X_1$ and $X_2$ may be generated as a result of performing, by the processor 110, each step of FIG. 9 on the two unmixed images $X_1$ and $X_2$, for example. The processor 110 may calculate the dependency between the plurality of unmixed images by calculating mutual information exemplified by Equation 8.

In a second embodiment in which the dependency between the plurality of unmixed images is evaluated based on the histogram generated with respect to the plurality of unmixed images, the processor 110 may evaluate the dependency by calculating a Kullback-Leibler divergence value between the plurality of unmixed images. "Kullback-Leibler divergence" is a function which may be used to calculate a difference between two different probability distributions. A value of the function indicates a difference between information entropies of different probability distributions. As the Kullback-Leibler divergence value is increased, a difference between the different probability distributions may be increased, and the different probability distributions may be well distinguished from each other. The Kullback-Leibler divergence value may be defined like Equation 9.

$$D_{KL}(X \| Y) = \sum_i X(i) \log \frac{X(i)}{Y(i)} \quad \text{[Equation 9]}$$

In Equation 9, X indicates a joint histogram or a joint probability distribution between the plurality of unmixed images. The joint histogram or the joint probability distribution between the plurality of unmixed images may be generated as a result of performing, by the processor 110, each step of FIG. 8 on the plurality of unmixed images, for example. Furthermore, Y indicates a marginal histogram or a marginal probability distribution between the plurality of unmixed images. The marginal histogram or the marginal probability distribution between the plurality of unmixed images may be generated as a result of performing, by the processor 110, each step of FIG. 9 on the plurality of unmixed images, for example. The processor 110 may calculate the dependency between the plurality of unmixed images based on a Kullback-Leibler divergence value exemplified by Equation 9.

In a third embodiment in which the dependency between the plurality of unmixed images is evaluated based on the histogram generated with respect to the plurality of unmixed images, the processor 110 may evaluate the dependency by calculating a cross-entropy value between the plurality of unmixed images. "Cross-entropy" means an average number of bits that is necessary to distinguish between two probability distributions, and a value thereof indicates a difference between different probability distributions. As the cross-entropy value is increased, a difference between the different probability distributions may be increased, and the different probability distributions may be well distinguished from each other. The cross-entropy value may be defined like Equation 10 and.

$$H(X, Y) = E_X[-\log Y] \quad \text{[Equation 10]}$$

In Equation 10, X indicates a joint histogram or a joint probability distribution between the plurality of unmixed images. The joint histogram or the joint probability distribution between the plurality of unmixed images may be generated as a result of performing, by the processor 110, each step of FIG. 8 on the plurality of unmixed images, for example. Furthermore, Y indicates a marginal histogram or a marginal probability distribution between the plurality of unmixed images. The marginal histogram or the marginal probability distribution between the plurality of unmixed images may be generated as a result of performing, by the processor 110, each step of FIG. 9 on the plurality of unmixed images, For example. The processor 110 may calculate the dependency between the plurality of unmixed images based on a cross-entropy value exemplified by Equation 10.

In a fourth embodiment in which the dependency between the plurality of unmixed images is evaluated based on the histogram generated with respect to the plurality of unmixed images, the processor 110 may evaluate the dependency by calculating a Rand index between the plurality of unmixed images. The "Rand-index" is a value indicative of similarity between two data sets. As the Rand-index is increased, a difference between the different two data sets may be increased, and different two data sets may be well distinguished from each other. For example, if it is assumed that two data sets X and Y are represented like X={$X_1, X_2$ to $X_i$} and Y={$Y_1, Y_2$ to $Y_j$}, respectively, an overlap between the two data sets may be indicated like Table 1.

TABLE 1

|   | $Y_1$ | $Y_2$ | ... | $Y_j$ | Sum |
|---|---|---|---|---|---|
| $X_1$ | $n_{11}$ | $n_{12}$ | ... | $n_{1j}$ | $a_1$ |
| $X_2$ | $n_{21}$ | $n_{22}$ | ... | $n_{2j}$ | $a_1$ |
| ⋮ | ⋮ | ⋮ | ⋱ | ⋮ | ⋮ |
| $X_i$ | $n_{i1}$ | $n_{i2}$ | ... | $n_{ij}$ | $a_i$ |
| Sum | $b_1$ | $b_2$ | ... | $b_j$ | |

For example, the data set X may include data of a joint histogram or a joint probability distribution between a plurality of unmixed images. The data set Y may include data of a marginal histogram or a marginal probability distribution between the plurality of unmixed images. A Rand-index based on Table 1 may be defined like Equation 11.

$$ARI = \frac{\sum_{i,j}\binom{n_{ij}}{2} - [\sum_i\binom{a_i}{2}\sum_j\binom{b_j}{2}]/\binom{n}{2}}{\frac{1}{2}[\sum_i\binom{a_i}{2} + \sum_j\binom{b_j}{2}] - [\sum_i\binom{a_i}{2} + \sum_j\binom{b_j}{2}]/\binom{n}{2}} \quad \text{[Equation 11]}$$

The processor 110 may calculate the dependency between the plurality of unmixed images based on a Rand-index exemplified by Equation 11.

The first embodiment to fourth embodiment relating to the dependence evaluation are merely examples for specifically describing a method of evaluating, by the processor 110, dependency between a plurality of unmixed images, and do not limit the present disclosure. The processor 110 of the present disclosure may evaluate dependency (or similarity) based on histograms generated with respect to a plurality of unmixed images by using various methods.

The server 100 according to the present disclosure may modify at least one parameter that is included in an unmixing matrix, based on a result of the dependence evaluation. Hereinafter, a detailed method of modifying a parameter is described with reference to the first embodiment to the fourth embodiment relating to the dependence evaluation.

In a first embodiment in which the dependency between the plurality of unmixed images is evaluated based on mutual information, the processor 110 may modify a parameter of the unmixing matrix in a way to decrease calculated mutual information. In the present disclosure, an expression "a parameter of the unmixing matrix is modified in a way to decrease a specific value calculated with respect to a plurality of unmixed images" may mean that as a result of modifying the parameter of the unmixing matrix, that is, a basis for generating a plurality of unmixed images from a plurality of mixed images, a specific value that is calculated from the plurality of unmixed images that are generated by using an unmixing matrix after the modification becomes smaller than a specific value that is calculated from the plurality of unmixed images that are generated by using an unmixing matrix before the modification. Hereinafter, the expression "a parameter of the unmixing matrix is modified in a way to decrease a specific value" may be interchangeably used with an expression "a parameter of the unmixing matrix is modified so that a specific value is decreased." The processor 110 may use a loss function, such as Equation 12, in order to modify a parameter of an unmixing matrix in a way to decrease mutual information. Equation 12 indicates a loss function in an embodiment according to Equation 8.

$$L_X(\alpha) = I(X_1 - \alpha \times X_2; X_2) \quad \text{[Equation 12]}$$
$$L_Y(\beta) = I(X_1; X_2 - \beta \times X_1)$$

In a second embodiment in which the dependency between the plurality of unmixed images is evaluated based on a Kullback-Leibler divergence value, the processor 110 may use a loss function, such as Equation 13, in order to modify a parameter of an unmixing matrix in a way to decrease the Kullback-Leibler divergence value. Equation 13 indicates a loss function in an embodiment according to Equation 9.

$$L_X(\alpha) = D_{KL}(X' \| Y) \quad \text{[Equation 13]}$$
$$L_Y(\beta) = D_{KL}(X \| Y')$$

If the plurality of unmixed images is assumed to be two, in Equation 13, X' may indicate a joint probability distribution that is determined between an image ($X_1 - \alpha \times X_2$) and an image $X_2$, and Y' may indicate a marginal probability distribution that is determined between an image $X_1$ and an image ($X_2 - \beta \times X_1$).

In a third embodiment in which the dependency between the plurality of unmixed images is evaluated based on a cross-entropy value, the processor 110 may use a loss function, such as Equation 14, in order to modify a parameter of an unmixing matrix in a way to decrease the cross-entropy value. Equation 14 indicates a loss function in an embodiment according to Equation 10.

$$L_X(\alpha) = H(X', Y) \quad \text{[Equation 14]}$$
$$L_Y(\beta) = H(X, Y')$$

If the plurality of unmixed images is assumed to be two, in Equation 14, X' may indicate a joint probability distribution that is determined between an image $(X_1-\alpha \times X_2)$ and an image $X_2$, and Y' may indicate a marginal probability distribution that is determined between an image $X_1$ and an image $(X_2-\beta \times X_1)$.

In a fourth embodiment in which the dependency between the plurality of unmixed images is evaluated based on a Rand-index, the processor 110 may use a loss function, such as Equation 15, in order to modify a parameter of an unmixing matrix in a way to decrease the Rand-index. Equation 15 indicates a loss function in an embodiment according to Equation 11.

$$L_X(\alpha) = ARI(X', Y) \quad \text{[Equation 15]}$$
$$L_Y(\beta) = ARI(X, Y')$$

If the plurality of unmixed images is assumed to be two, in Equation 15, X' may indicate a joint probability distribution that is determined between an image $(X_1-\alpha \times X_2)$ and an image $X_2$, and Y' may indicate a marginal probability distribution that is determined between an image $X_1$ and an image $(X_2-\beta \times X_1)$.

The processor 110 may determine at least one parameter (e.g., $\alpha$ or $\beta$ in Equations 12 to 15) that minimizes various loss functions, such as Equations 12 to 15, based on Equation 16.

$$\hat{\alpha} = \arg\min_{\alpha} L_1(\alpha) \quad \text{[Equation 16]}$$
$$\hat{\beta} = \arg\min_{\beta} L_2(\beta)$$

As described above, the server 100 according to the present disclosure may modify at least one parameter that is included in an unmixing matrix, based on a result of the dependence evaluation.

According to some additional embodiments of the present disclosure, the processor 110 may evaluate dependency between a plurality of unmixed images based on an artificial neural network model, and may modify a parameter of an unmixing matrix based on a result of the dependence evaluation. A method of modifying, by the processor 110, a parameter of an unmixing matrix based on an artificial neural network model according to the present disclosure is specifically described with reference to a drawing.

Next, the processor 110 may determine whether a predetermined threshold condition is satisfied (S1145).

In an embodiment, the predetermined threshold condition may be a condition according to an update count of the unmixing matrix. For example, it is assumed that the predetermined threshold condition is a condition that is satisfied when the unmixing matrix is modified by N (N is a natural number equal to or greater than 1). In this case, the processor 110 may count an update count whenever the unmixing matrix is updated, and may determine that the predetermined threshold condition is satisfied when the counted update count is N times.

In an embodiment in which the processor 110 calculates a dependence evaluation value between a plurality of unmixed images, the predetermined threshold condition may be a condition based on the size of a calculated dependence evaluation value. For example, it is assumed that the predetermined threshold condition is satisfied when the size of a dependence evaluation value calculated between a plurality of unmixed images is 0.2 or less. In this case, the processor 110 may determine the predetermined threshold condition is satisfied when the size of the dependence evaluation value calculated between the plurality of unmixed images as a result of performing step S1130 is 0.2 or less.

Furthermore, in an embodiment in which the processor 110 evaluates dependency based on an artificial neural network model, the predetermined threshold condition may be a condition based on at least one of the number of times of learning by the artificial neural network model, the size of an output value, or a loss value (an error between an output value and a ground truth). For example, it is assumed that the predetermined threshold condition is a condition that is satisfied when a loss value of the artificial neural network model is 0.1 or less. In this case, when the loss value of the artificial neural network model is 0.1 or less, the processor 110 may determine that the predetermined threshold condition is satisfied.

If the predetermined threshold condition is not satisfied as a result of determining, by the processor 110, whether the predetermined threshold condition is satisfied, the processor 110 may repeatedly perform steps S1120 to S1140 until the predetermined threshold condition is satisfied.

If the predetermined threshold condition is satisfied as a result of determining, by the processor 110, whether the predetermined threshold condition is satisfied, the processor 110 may terminate the update of the unmixing matrix. The update unmixing matrix may be a matrix at least one parameter of which has been modified compared to the unmixing matrix before the update.

Figure 12:
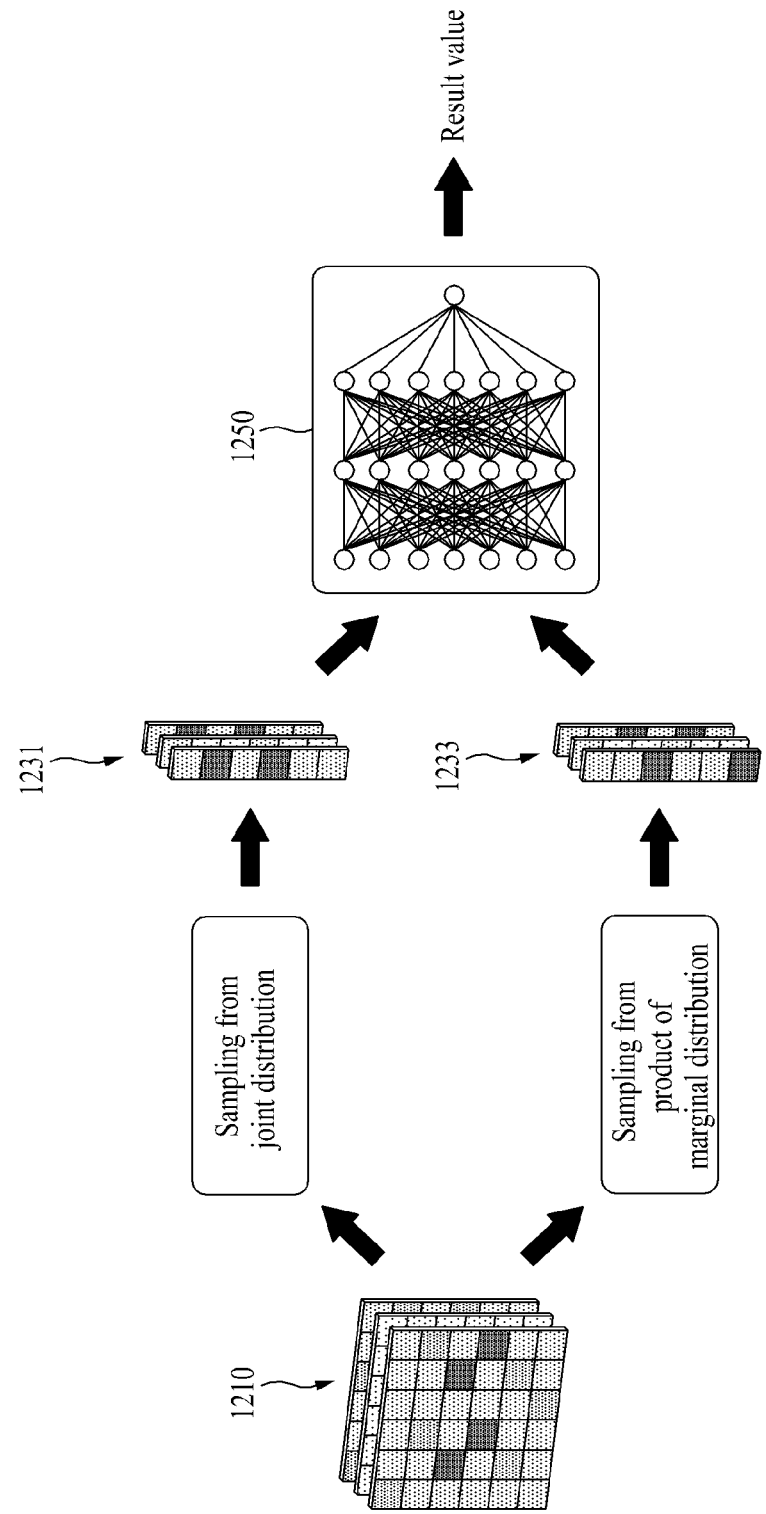
FIG. 12 is a concept view conceptually illustrating a process of evaluating dependency between a plurality of unmixed images based on an artificial neural network model according to an embodiment of the present disclosure.

FIG. 12 is a concept view conceptually illustrating a process of evaluating dependency between a plurality of unmixed images 1210 based on an artificial neural network model 1250 according to an embodiment of the present disclosure. The artificial neural network model 1250 may be an artificial neural network model (hereinafter also referred to as a "classification model") that receives input data and generates output data for determining the type of input data. Hereinafter, it is assumed and described that the plurality of unmixed images 1210 includes three unmixed images for convenience of description with reference to FIG. 12, but the present disclosure is not limited thereto.

The processor 110 may generate at least one input data that is input to the artificial neural network model 1250, based on the plurality of unmixed images 1210. In an embodiment, the processor 110 may generate the input data by sampling data from at least one of two or more different probability distributions relating to the plurality of unmixed images 1210. In the present disclosure, the term "sampling" may be a term for denoting an operation of selecting or extracting a given number of elements based on a probability value of each element that is included in a specific probability distribution. For example, if a first element that is included in a specific probability distribution has a higher probability value than a second element and one element is sampled from the specific probability distribution, the probability that the first element will be selected may be higher than the probability that the second element will be selected. Furthermore, for example, if all elements included in a specific probability distribution have the same probability value and one element is sampled from a specific probability distribution, the probability that all the elements will be selected may be the same. In the present disclosure, a probability distribution for sampling, by the processor 110, data may be a probability distribution (hereinafter also referred to as a "first probability distribution") that is determined based on values of pixels at the same location, which are included in plurality of unmixed images 1210, respectively, for example. The first probability distribution may be determined by performing, by the processor 110, the method described with reference to FIG. 8 on the plurality of unmixed images 1210. The processor 110 may generate one input data by sampling data from the first probability distribution. Furthermore, a probability distribution for sampling, by the processor 110, data may be a probability distribution (hereinafter also referred to as a "second probability distribution") that is determined based on values of pixels at different locations, which are included in the plurality of unmixed images 1210, respectively, for example. The second probability distribution may be determined by performing, by the processor 110, the method described with reference to FIG. 9 on the plurality of unmixed images 1210. The processor 110 may generate one input data by sampling the second probability distribution from data.

In an embodiment, input data 1231 that is sampled from the first probability distribution may be represented like Equation 17.

$$x = (\{(x_{1i}, x_{2i}, x_{3i})\}_{i=1}^{n} \sim (P_{X_1 X_2 X_3}(x_1, x_2, x_3)))^n \quad \text{[Equation 17]}$$

In Equation 17, x on the left side indicates at least one input data that is sampled from the first probability distribution, and $P_{X_1 X_2 X_3}(x_1, x_2, x_3)$ on the right side indicates the first probability distribution corresponding to a joint probability distribution of the plurality of unmixed images 1210. Furthermore, $X_1$, $X_2$ and $X_3$ of $P_{X_1 X_2 X_3}(x_1, x_2, x_3)$ denote probability variables corresponding to unmixed images included in the plurality of unmixed images 1210, respectively. $x_1$, $x_2$, and $x_3$ denote realized values or pixel values of the probability variables $X_1$, $X_2$ and $X_3$, respectively. Furthermore, $(x_{1i}, x_{2i}, x_{3i})$ indicates i-th input data (i is a natural number of 1 or more to n or less) sampled from the first probability distribution, $x_{1i}$ denotes a pixel value extracted from the first unmixed image among the plurality of unmixed images 1210, $x_{2i}$ denotes a pixel value extracted from the second unmixed image among the plurality of unmixed images 1210, and, $x_{3i}$ denotes a pixel value extracted from the third unmixed image among the plurality of unmixed images 1210. In this case, since the first probability distribution is determined based on values of pixels at the same location, which are included in the plurality of unmixed images 1210, respectively, the pixel values included in $(x_{1i}, x_{2i}, x_{3i})$ may be values that are determined from the pixels at the same location that correspond to each other in the plurality of unmixed images. Equation 17 is an exemplary description for specifically describing the input data 1231 that is sampled from the first probability distribution, and does not limit the present disclosure.

In an embodiment, input data 1233 that is sampled from the second probability distribution may be represented like Equation 18.

$$x' = (\{(x'_{1i}, x'_{2i}, x'_{3i})\}_{i=1}^{n} \sim (P_{X_1}(x_1) P_{X_2}(x_2) P_{X_3}(x_3)))^n \quad \text{[Equation 18]}$$

In Equation 18, x' on the left side indicates at least one input data that is sampled from the second probability distribution, and $P_{X_1}(x_1) P_{X_2}(x_2) P_{X_3}(x_3)$ on the right side indicates the second probability distribution corresponding to a marginal probability distribution of the plurality of unmixed images 1210. Furthermore, $X_1$, $X_2$ and $X_3$ in $P_{X_1}(x_1) P_{X_2}(x_2) P_{X_3}(x_3)$ denote probability variables corresponding to unmixed images that are included in the plurality of unmixed images 1210, respectively, and $x_1$, $x_2$ and $x_3$ denote realized values or pixel values of the probability variables $X_1$, $X_2$ and $X_3$, respectively. Furthermore, $(x_{1i}', x_{2i}', x_{3i}')$ indicates i-th input data (i is a natural number of 1 or more to n or less) sampled from the second probability distribution, $x_{1i}'$ may denote a pixel value extracted from the first unmixed image among the plurality of unmixed images 1210, $x_{2i}'$ may denote a pixel value extracted from the second unmixed image among the plurality of unmixed images 1210, and $x_{3i}'$ may denote a pixel value extracted from the third unmixed image among the plurality of unmixed images 1210. In this case, since the second probability distribution is determined based on values of pixels at different locations, which are included in the plurality of unmixed images 1210, respectively, the pixel values included in $(x_{1i}', x_{2i}', x_{3i}')$ may be values determined from pixels at different locations in the plurality of unmixed images. Equation 18 is merely an exemplary description for specifically describing the input data 1233 that is sampled from the second probability distribution, and do not limit the present disclosure.

In an embodiment, the processor 110 may input the input data to the classification model, and may determine the type of input data based on output data of the classification model. If the input data is data sampled based on one of two or more probability distributions that are differently determined in relation to a plurality of unmixed images, the classification model may generate output data for determining a specific probability distribution, that is, a source of the input data. For example, the input data for the classification model may be the input data 1231 that is sampled from the first probability distribution or the input data 1233 that is sampled from the second probability distribution. In this case, the output data of the classification model may be data that determines which of the probability distributions are associated with the input data. That is, if the input data is the input data 1231 that is sampled from the first probability distribution, the classification model may output information indicative of the first probability distribution as output data for the corresponding input data. Furthermore, if the input data is the input data 1233 that is sampled from the second probability distribution, the classification model may output information indicative of the second probability distribution as output data for the input data.

In order to train the artificial neural network model 1250 as the classification model according to an embodiment of the present disclosure, the processor 110 may generate learning data by differently labeling the input data 1231 that is sampled from the first probability distribution and the input data 1233 that is sampled from the second probability distribution. For example, the processor 110 may label, with "1" as a ground truth, the input data 1231 that is sampled from the first probability distribution, and may label, with "0" as a ground truth, the input data 1233 that is sampled from the second probability distribution. If the classification model is trained based on the learning data described above, the processor 110 may train the classification model by inputting, to the classification model, input data included in the learning data, obtaining output data (e.g., a real number between 0 and 1) output by the classification model, and updating a value of at least one parameter included in the classification model through a back propagation scheme based on a difference between a ground truth labeled with respect to corresponding input data and the output data of the classification model.

Figure 13:
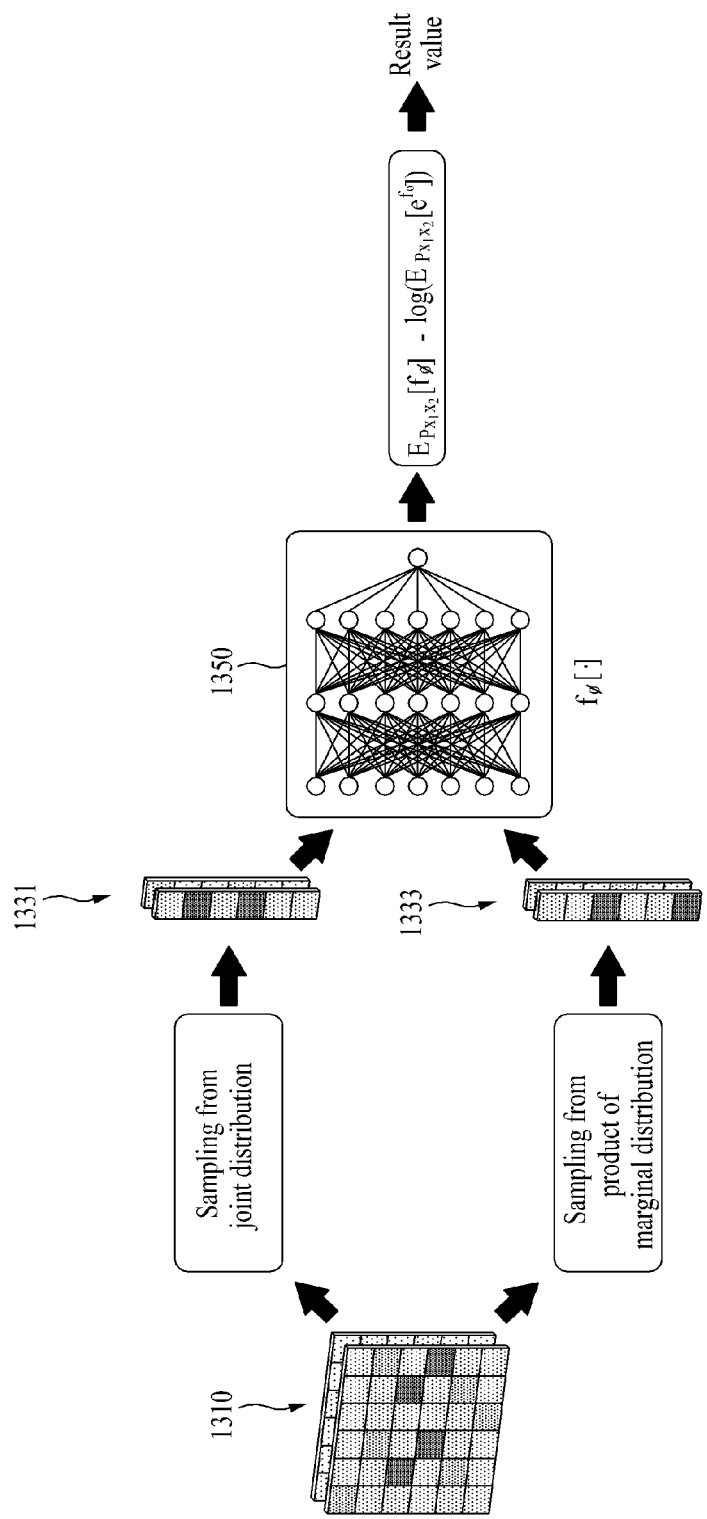
FIG. 13 is a concept view conceptually illustrating a process of evaluating dependency between a plurality of unmixed images based on an artificial neural network model according to another embodiment of the present disclosure.

FIG. 13 is a concept view conceptually illustrating a process of evaluating dependency between a plurality of unmixed images 1310 based on an artificial neural network model 1350 according to another embodiment of the present disclosure. The artificial neural network model 1350 may be an artificial neural network model (hereinafter also referred to as a "prediction model") that receives a plurality of input data and generates output data for predicting a specific value related to the plurality of input data. Hereinafter, it is assumed and described that the plurality of unmixed images 1310 includes two unmixed images for convenience of description with reference to FIG. 13, but the present disclosure is not limited thereto.

The processor 110 may generate a plurality of input data input to the artificial neural network model 1350, based on the plurality of unmixed images 1310. The processor 110 may generate the plurality of input data sampled from different probability distributions that are determined based on the plurality of unmixed images 1310, respectively. Hereinafter, it is assumed and described that the artificial neural network model 1350 receives two input data, but this does not limit the present disclosure. The artificial neural network model 1350 of the present disclosure may receive three or more input data. In an embodiment, the processor 110 may generate two input data by sampling data from each of two different probability distributions relating to the plurality of unmixed images 1310. The two different probability distributions relating to the plurality of unmixed images 1310 may be a probability distribution (hereinafter also referred to as a "third probability distribution") that is determined based on values of pixels at the same location, which are included in the plurality of unmixed images 1310, respectively, or a probability distribution (hereinafter also referred to as a "fourth probability distribution") that is determined based on values of pixels at different locations, which are included in the plurality of unmixed images 1310, respectively, for example. In this case, the third probability distribution may be determined by performing, by the processor 110, the method described with reference to FIG. 8 on the plurality of unmixed images 1310. The fourth probability distribution may be determined by performing, by the processor 110, the method described with reference to FIG. 9 on the plurality of unmixed images 1310. The processor 110 may generate a plurality of input data input to the artificial neural network model 1350 by sampling input data 1331 from the third probability distribution and sampling input data 1333 from the fourth probability distribution.

The processor 110 may input the plurality of input data to the artificial neural network model 1350, and may obtain a specific value that is predicted by the artificial neural network model 1350 and that is related to the plurality of input data. The "specific value" that is predicted by the artificial neural network model 1350 and that is related to the plurality of input data may denote a value that is output by the artificial neural network model 1350 that has received the plurality of input data.

The processor 110 may calculate a dependence evaluation value for a plurality of unmixed images based on the obtained specific value. The type of dependence evaluation value that is calculated by the processor 110 based on the artificial neural network model may be determined according to various embodiments as described above. Hereinafter, for convenience of description, as an example of the dependence evaluation value calculated based on the artificial neural network model, an example in which the processor 110 calculates the aforementioned "mutual information" is assumed. In an embodiment, mutual information between a plurality of unmixed images, which is calculated based on a specific value predicted by a prediction model, may be represented like Equation 19.

$$I(x; x') = \sup_{\phi} \mathbb{E}_{P_{X_1 X_2}}[f_\phi] - \log(\mathbb{E}_{P_{X_1} P_{X_2}}[e^{f_\phi}])$$ [Equation 19]

In Equation 19, I(x; x') on the left side indicates mutual information between two unmixed images (i.e., $X_1$ and $X_2$), which is calculated based on two input data (i.e., x and x') input to the artificial neural network model 1350. In $f_\phi$ on the right side, $\phi$ indicates at least one parameter included in the prediction model. $f_\phi$ is output data of the prediction model and indicates a specific value related to the two input data. Furthermore, in $$\mathbb{E}_{P_{X_1 X_2}}[f_\phi],$$

$P_{X_1 X_2}$ indicates a joint probability distribution of the plurality of unmixed images 1310.

$$\mathbb{E}_{P_{X_1 X_2}}[f_\phi]$$

indicates an expected value of a specific value ($f_\phi$) output by the prediction model with respect to the two input data (x and x') in the joint probability distribution of the plurality of unmixed images 1310. $P_{X_1} P_{X_2}$ in $$\mathbb{E}_{P_{X_1} P_{X_2}}[e^{f_\phi}]$$

indicates the product of marginal probability distributions of the plurality of unmixed images 1310, respectively.

$$\sup_{\phi}(\cdot)$$

indicates the upper limit of a term within parentheses according to a change in the value $\phi$. As illustrated through Equation 19, the processor 110 may calculate mutual information for the plurality of unmixed images based on the specific value that is predicted by the prediction model. For example, as the third probability distribution and the fourth probability distribution corresponding to the two input data (x and x'), respectively, are more similar to each other, the mutual information (I(x; x')) between the two input data may have a greater value. Furthermore, as mutual information is increased, two unmixed images may be interpreted as more dependent images.

In order to train the artificial neural network model 1350 as the aforementioned prediction model, the processor 110 may calculate mutual information based on a specific value that is output by the prediction model, and may train the prediction model so that the calculated mutual information is maximized. That is, when the prediction model predicts a specific value for a plurality of input data that are sampled from a plurality of unmixed images, a value of at least one parameter included in the prediction model may be updated so that the specific value is predicted in a way that mutual information for the plurality of unmixed images is maximized. For example, the processor 110 may update a value of at least one parameter included in the prediction model according to a chain rule by applying a gradient descent method (or a gradient ascent method) to a predetermined mutual information calculation equation.

The unmixing matrix and the artificial neural network model of the present disclosure may be adversarially trained. In the present disclosure, the expression that two objects are "adversarially trained" may mean that the two objects are trained to solve conflicting tasks and thus a value of at least one parameter included in each object is changed.

In an embodiment relating to the adversarial training according to the present disclosure, if the artificial neural network model corresponds to a classification model, a value of at least one element included in the unmixing matrix may be updated so that first input data and second input data input to the classification model are rarely distinguished from each other by the artificial neural network model and a value of at least one parameter included in the artificial neural network model may be updated so that first input data and second input data are well distinguished from each other by the artificial neural network model. For example, the first input data may be data sampled from a first probability distribution, and the second input data may be data sampled from a second probability distribution. As described above, the classification model may be an artificial neural network model that receives a plurality of input data sampled from probability distributions differently determined from a plurality of unmixed images, respectively, and determines a probability distribution associated with each input data. Furthermore, the unmixing matrix may generate a plurality of unmixed images, that is, a basis for generating each input data. That is, the unmixing matrix may generate the plurality of unmixed images from a plurality of mixed images. The classification model may determine the type of input data that is sampled from each of the plurality of unmixed images. Accordingly, the classification model is trained so that a plurality of input data is well distinguished from each other. In contrast, the unmixing matrix is trained so that a plurality of input data sampled from a plurality of unmixed images is rarely distinguished from each other by the classification model. Accordingly, the classification model and the unmixing matrix can be adversarially trained.

In an embodiment, if two types of input data input to the classification model are well distinguished from each other by the classification model, the processor 110 may determine that the training of the classification model is insufficient, and may additionally perform the training of the classification model. In this case, a plurality of unmixed images generated from a plurality of mixed images by using an unmixing matrix may be determined to be mutually dependent. In contrast, if two types of input data input to the classification model are rarely distinguished from each other by the classification model, the processor 110 may determine that the training of the classification model is sufficient, and may stop the training of the classification model. In this case, a plurality of unmixed images generated from a plurality of mixed images by using an unmixing matrix may be determined to be mutually independent.

In the present disclosure, the expression "two types of input data input to the classification model are well distinguished from each other by the classification model" or "two types of input data input to the classification model are rarely distinguished from each other by the classification model" may be determined quantitatively or numerically. For example, when the classification model generates output data for determining the type of input data, the processor 110 may evaluate the accuracy (or reliability) of the classification model by using a test data set labeled with a ground truth with respect to a given number of input data. Specifically, if the classification result of the processor 110 for more than a certain number or percentage of the input data in the test dataset is within a tolerance from a ground truth, the processor 110 may determine that the training of the classification model is sufficient. Alternatively, if a change in the accuracy of the classification model as training is performed is equal to or less than a threshold value, the processor 110 may determine that the training of the classification model is sufficient. The method of evaluating the accuracy of the classification model is merely an example for a description, and does not limit the present disclosure.

In another embodiment related to the adversarial trained according to the present disclosure, if the artificial neural network model corresponds to the prediction model, a value of at least one parameter included in the prediction model may be updated so that a specific value is predicted in a way that a dependence evaluation value (e.g., mutual information, a Kullback-Leibler divergence value, a cross-entropy value, or a Rand-index) for a plurality of unmixed images is maximized. A value of at least one element included in the unmixing matrix may be updated so that a plurality of unmixed images is generated in a way that a dependence evaluation value for the plurality of unmixed images is minimized. The prediction model may be an artificial neural network model that receives a plurality of input data sampled based on probability distributions differently determined from a plurality of unmixed images, respectively, as described above and that predicts a specific value related to the plurality of input data. Furthermore, the unmixing matrix may generate the plurality of unmixed images, that is, a basis for generating the plurality of input data. That is, the unmixing matrix may generate the plurality of unmixed images from a plurality of mixed images. The prediction model may receive the plurality of input data sampled from the plurality of unmixed images, respectively, and may predict a specific value related to the plurality of input data. Furthermore, the specific value predicted by the prediction model may be a value, that is, a basis for calculating a dependence evaluation value for the plurality of unmixed images. Accordingly, the prediction model is trained in a way that a dependence evaluation value for a plurality of unmixed images is maximized, and the unmixing matrix is trained in a way that a dependence evaluation value for the plurality of unmixed images is minimized. Accordingly, the prediction model and the unmixing matrix may be adversarially trained.

In an embodiment, if a dependence evaluation value calculated based on a specific value output by the prediction model is not greater than a predetermined threshold value, the processor 110 may determine that the training of the prediction model is insufficient, and may additionally perform the training of the prediction model. In this case, a plurality of unmixed images generated from a plurality of mixed images by using an unmixing matrix may be determined to be mutually dependent. In contrast, if a dependence evaluation value calculated based on a specific value output by the prediction model is greater than the predetermined threshold value, the processor 110 may determine that the training of the prediction model is sufficient, and may stop the training of the prediction model. In this case, a plurality of unmixed images generated from a plurality of mixed images by using an unmixing matrix may be determined to be mutually independent. The processor 110 may determine a degree of the training of the prediction model based on the number of times that the prediction model is trained, for example, the number of learning epochs.

According to the some embodiments of the present disclosure, the processor 110 may evaluate dependency between a plurality of unmixed images, and may determine a parameter of an unmixing matrix based on a result of the evaluation. The processor 110 according to the present disclosure may generate an unmixed image of each biomolecule that is included in a sample from a plurality of mixed images obtained by photographing the sample, based on the unmixing matrix determined as described above.

Hereinafter, a method of obtaining a plurality of mixed images according to an embodiment of the contents of the present disclosure is described.

As described above with reference to FIG. 4, a conventional method of obtaining an image of each biomolecule in a sample including some biomolecules has a limit that emission spectra of fluorescent materials labeling respective biomolecules should not overlap as much as possible. Accordingly, there is a limit that only a maximum of four fluorescent materials can be simultaneously used. Furthermore, after images of the four biomolecules included in the sample are obtained by using the four fluorescent materials, in order to subsequently obtain an image of another biomolecule included in the sample, a post-processing process of removing the existing fluorescent material needs to be performed before the another biomolecule is newly labeled. The post-processing process of removing a fluorescent material may include a process of deactivating a fluorescent material, or a process of detaching an antibody labeled with a fluorescent material or a material used to label a biomolecule with a fluorescent material, for example.

In contrast, the method of processing an image according to the present disclosure does not require the process of inactivating or removing a fluorescent material, which is required for the conventional method. Accordingly, in an embodiment of the present disclosure, a plurality of mixed images may be obtained differently from the conventional method.

A plurality of mixed images according to an embodiment of the present disclosure may be sequentially generated by performing one or more rounds, where each round involves staining and photographing of a sample. Furthermore, a plurality of mixed images according to the present disclosure may be sequentially generated by performing one or more rounds, where each round involves staining and photographing without a post-processing process of removing a fluorescent material. As described above, the method of processing an image according to the present disclosure has an effect in that an unmixed image of each biomolecule can be generated more rapidly and effectively by generating a plurality of unmixed images without a conventional process of removing a fluorescent material.

Figure 14:
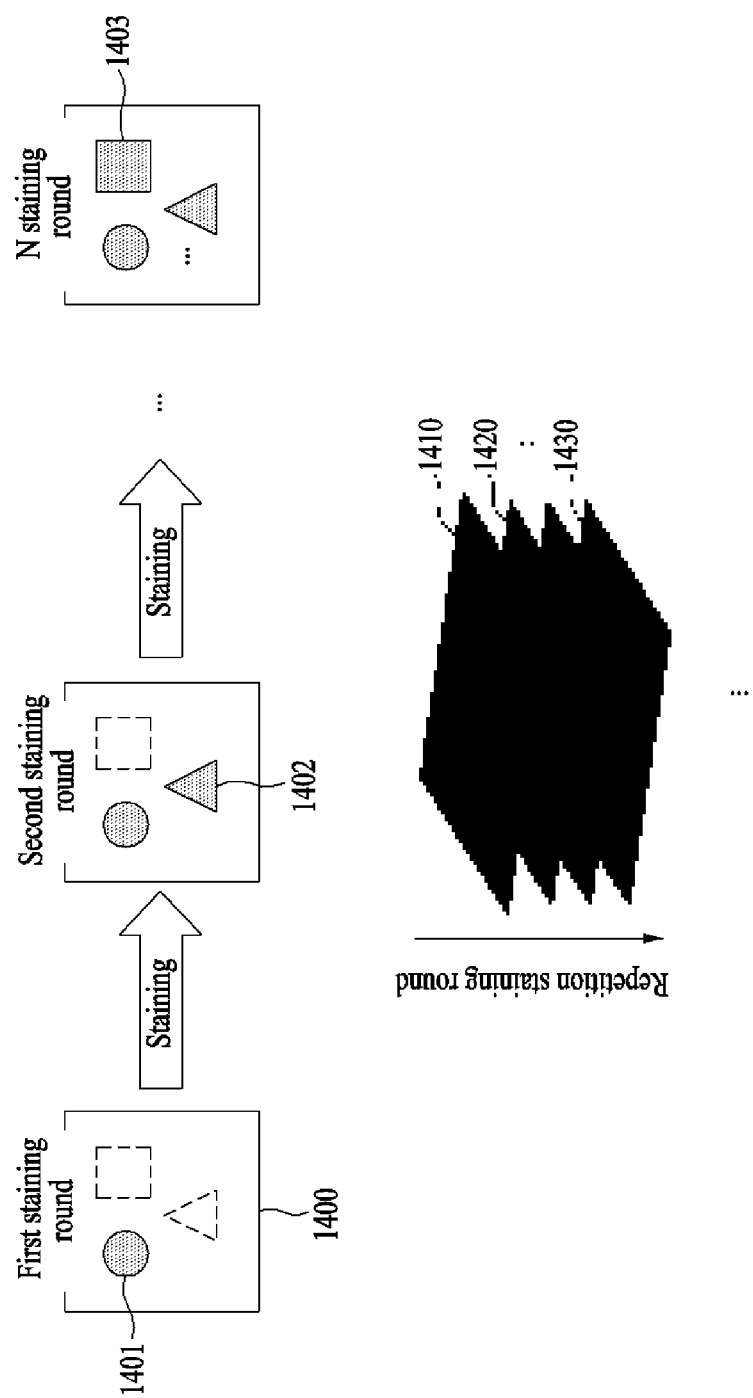
FIG. 14 is a concept view illustrating a process of sequentially obtaining a plurality of images according to an embodiment of the present disclosure.

FIG. 14 is a concept view illustrating a process of sequentially obtaining a plurality of images according to an embodiment of the present disclosure. In FIG. 14, it is assumed that a sample 1400 includes N (N is a natural number equal to or greater than 1) biomolecules. In this case, when a first biomolecule 1401 included in the sample 1400 is labeled according to first staining round, the processor 110 may obtain a first mixed image 1410 by photographing the sample 1400 after the first staining round through the photographing unit. The first biomolecule 1401 labeled according to the first staining round may be indicated on the first mixed image 1410, and the remaining biomolecules that have not been labeled may not be indicated on the first mixed image 1410. Next, when a second biomolecule 1402 included in the sample 1400 is labeled according to second staining round, the processor 110 may obtain a second mixed image 1420 by photographing the sample 1400 after the second staining round through the photographing unit. The first biomolecule 1401 labeled according to the first staining round and the second biomolecule 1402 labeled according to the second staining round may be indicated on the second mixed image 1420, and the remaining biomolecules that have not been labeled may not be indicated on the second mixed image 1420. If an N-th biomolecule 1403 included in the sample 1400 is labeled according to N-th staining round by repeating such a process, the processor 110 may obtain an N-th mixed image 1430 by photographing the sample 1400 after the N-th staining round through the photographing unit. The first biomolecule 1401 labeled according to the first staining round, the second biomolecule 1402 labeled according to the second staining round, and the N-th biomolecule 1403 labeled according to the N-th staining round may be included in the N-th mixed image 1430. If a plurality of mixed images is sequentially obtained as described above, another biomolecule may be further represented in a mixed image obtained after an "(i+1)" staining round, compared to a mixed image obtained after an "i" staining round. Hereinafter, in the present disclosure, when compared to the mixed image obtained after the "i" staining round, one biomolecule additionally represented on the mixed image obtained after the "(i+1)" staining round may be denoted as a "biomolecule labeled in an (i+1)-th staining round" (i is a natural number equal to or greater than 1). For example, when compared to the first mixed image 1410 in FIG. 14, the second biomolecule 1402 additionally represented on the second mixed image 1420 may be denoted as a "biomolecule labeled in a second staining round." When compared to an (N−1)-th mixed image, the N-th biomolecule 1403 additionally represented on the N-th mixed image 1430 may be denoted as a "biomolecule labeled in an N staining round."

The method of processing an image according to the present disclosure may generate an unmixed image of a specific biomolecule based on two or more consecutive mixed images, among a plurality of mixed images that are sequentially obtained, as described with reference to FIG. 14. In the present disclosure, an expression, such as "two or more mixed images that are consecutively sequentially obtained" or "two or more mixed images obtained by sequentially staining a plurality of biomolecules included in a sample", may mean two or more mixed images obtained by sequentially performing a round, including staining and photographing for a biomolecule, on a plurality of biomolecules that are included in a sample. For example, two mixed images that are consecutively sequentially obtained may include a mixed image that is photographed after i-th (i is a natural number equal to or greater than 1) staining round and a mixed image that is photographed after (i+1)-th staining round. Furthermore, for example, three mixed images that are consecutively sequentially obtained may include a mixed image that is photographed after i-th staining round, a mixed image that is photographed after (i+1)-th staining round, and a mixed image that is photographed after (i+2)-th staining round. Hereinafter, for convenience of description, an expression "a plurality of mixed images that are consecutively sequentially obtained" and an expression "a plurality of consecutive mixed images" may be interchangeably used.

Figure 15:
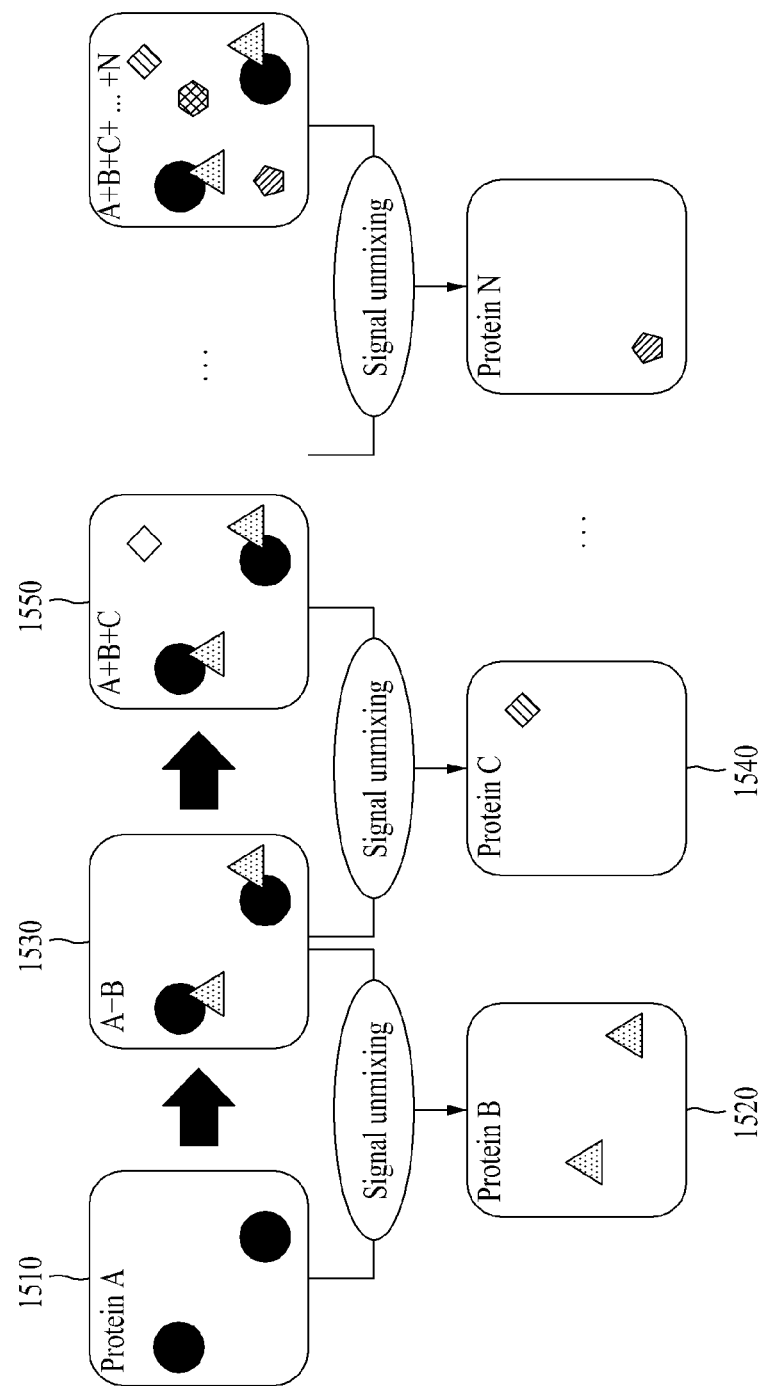
FIG. 15 is a concept view exemplarily illustrating a method of obtaining an unmixed image of at least one biomolecule from two consecutive mixed images among a plurality of mixed images that are sequentially obtained according to an embodiment of the present disclosure.

FIG. 15 is a concept view exemplarily illustrating a method of obtaining an unmixed image of at least one biomolecule from two consecutive mixed images, among a plurality of mixed images that are sequentially obtained, according to an embodiment of the present disclosure. The processor 110 according to the present disclosure may generate an unmixed image of a biomolecule labeled in an "(i+1)" staining round, by performing an operation on two consecutive mixed images, that is, a mixed image obtained after "i" staining round and a mixed image obtained after "(i+1)" staining round.

In an embodiment, the processor 110 may obtain a first mixed image 1510 by staining a biomolecule (e.g., protein A) included in a sample according to first staining round and photographing the sample. Furthermore, the processor 110 may obtain a second mixed image 1530 by staining another biomolecule (e.g., protein B) included in the sample according to subsequent second staining round and photographing the sample. Furthermore, the processor 110 may obtain a third mixed image 1550 by staining another biomolecule (e.g., protein C) included in the sample according to subsequent third staining round and photographing the sample. The processor 110 may perform an operation on two consecutive mixed images based on at least one parameter, and may generate an unmixed image of at least one biomolecule. For example, the processor 110 may generate an unmixed image 1520 of the biomolecule (i.e., protein B) labeled in the second staining round process by performing an operation on the first mixed image 1510 and the second mixed image 1530. Furthermore, the processor 110 may generate an unmixed image 1540 of the biomolecule (i.e., protein C) labeled in the third staining round by performing an operation on the second mixed image 1530 and the third mixed image 1550. The unmixed image of the biomolecule (i.e., protein A) labeled in the first staining round may be obtained as the first mixed image 1510.

Figure 16:
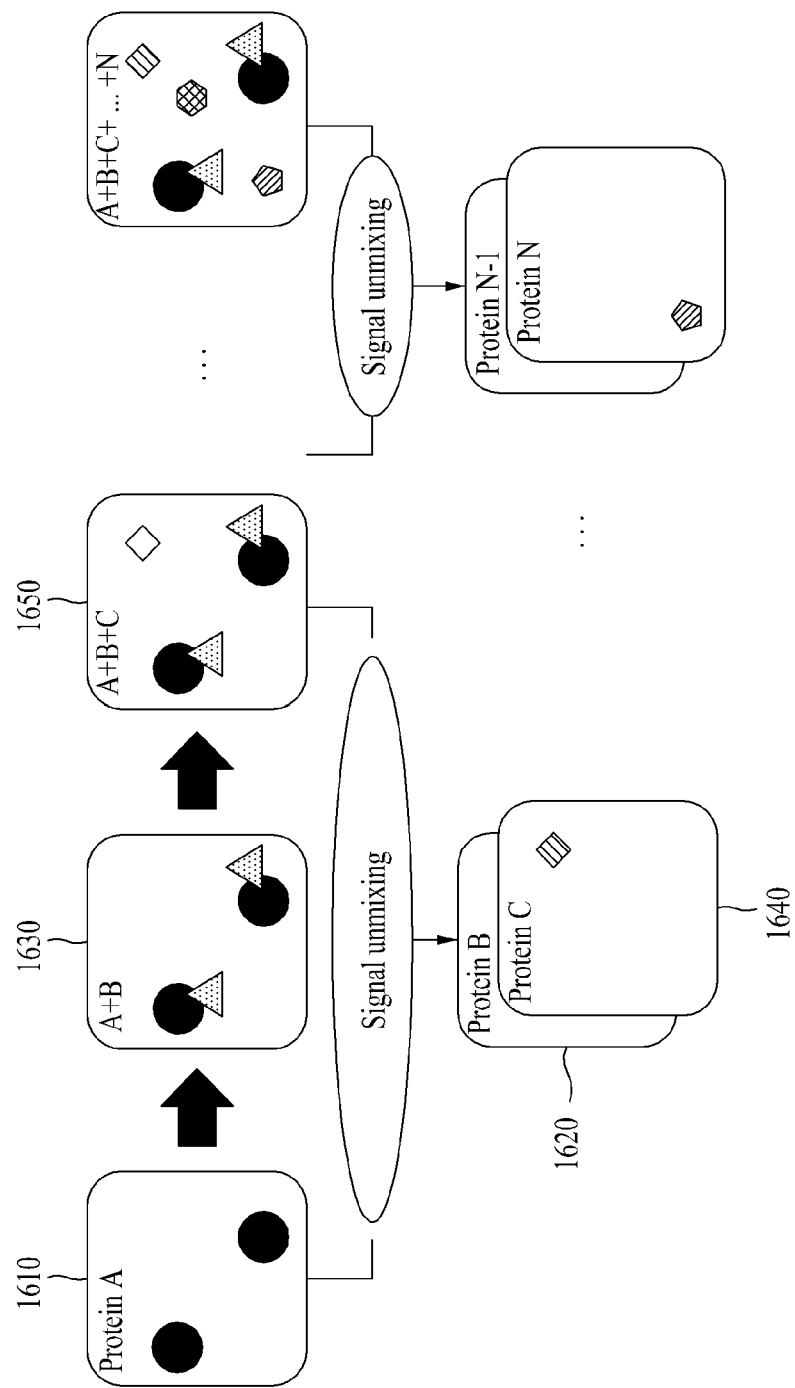
FIG. 16 is a concept view exemplarily illustrating a method of obtaining an unmixed image of at least two biomolecules from three consecutive mixed images among a plurality of mixed images that are sequentially obtained according to an embodiment of the present disclosure.

FIG. 16 is a concept view exemplarily illustrating a method of obtaining an unmixed image of at least two biomolecules from three consecutive mixed images, among a plurality of mixed images that are sequentially obtained, according to an embodiment of the present disclosure. A first mixed image 1610, a second mixed image 1630, and a third mixed image 1650 illustrated in FIG. 16 may be obtained in the same manner as the first mixed image 1510, the second mixed image 1530, and the third mixed image 1550 illustrated in FIG. 15, respectively. The processor 110 may perform an operation on the three consecutive mixed images based on at least one parameter, and may generate unmixed images of at least two biomolecules, respectively. For example, the processor 110 may generate an unmixed image 1620 of a biomolecule (i.e., protein B) labeled in a second staining round and an unmixed image 1640 of a biomolecule (i.e., protein C) labeled in a third staining round by simultaneously processing the first mixed image 1610, the second mixed image 1620, and the third mixed image 1630. An unmixed image of a biomolecule (i.e., protein A) labeled in a first round staining process may be obtained as the first mixed image 1610.

A method of obtaining an unmixed image of a biomolecule based on two or three consecutive mixed images has been described above with reference to FIG. 15 or 16, but this does not limit the present disclosure. In the present disclosure, an unmixed image of a biomolecule may be generated based on a given number of two or more consecutive mixed images. Hereinafter, a method of obtaining an unmixed image based on two consecutive mixed images is described, for convenience of description.

Figure 17:
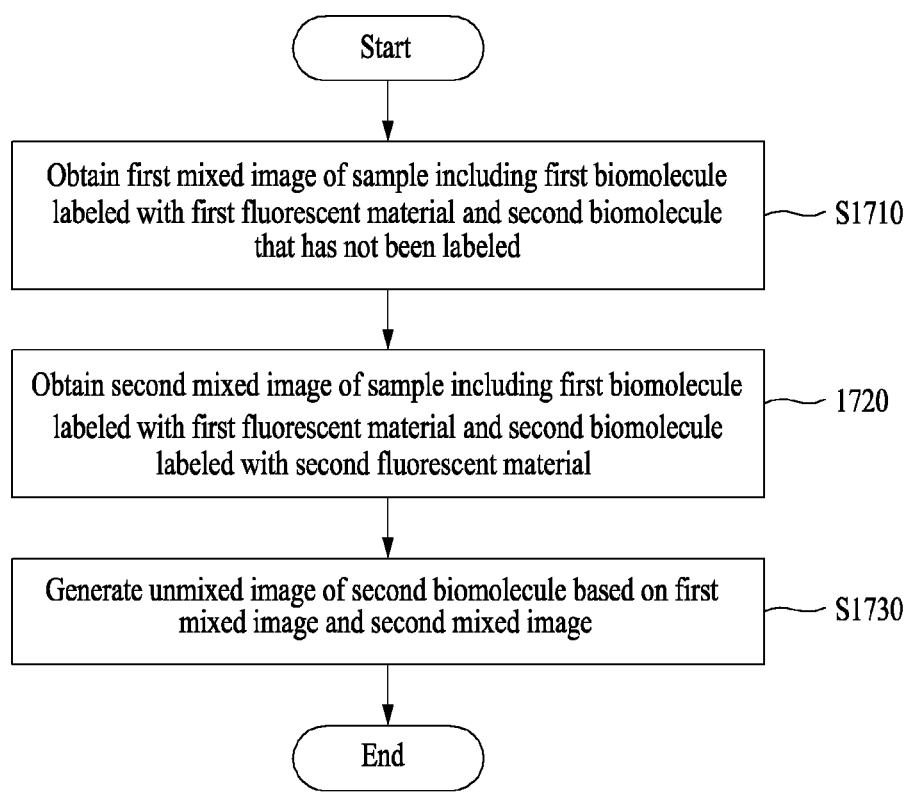
FIG. 17 is a flowchart illustrating an operation of the server generating an unmixed image of at least one biomolecule based on two consecutive mixed images according to an embodiment of the present disclosure.

FIG. 17 is a flowchart illustrating an operation of the server 100 generating an unmixed image of at least one biomolecule based on two consecutive mixed images according to an embodiment of the present disclosure.

The processor 110 may obtain a first mixed image of a sample including a first biomolecule labeled with a first fluorescent material and a second biomolecule that has not been labeled (S1710). In the embodiment of FIG. 17, the first biomolecule may be a biomolecule labeled with a specific fluorescent material in an i-th staining round (i.e., an i staining round) for the sample. The processor 110 may obtain a mixed image by obtaining the mixed image of a sample in which a first biomolecule has been labeled through a photographing unit (not illustrated) or receiving the mixed image of the sample in which the first biomolecule has been labeled from an external device or the user terminal 200.

Next, the processor 110 may obtain a second mixed image of the sample including the first biomolecule labeled with the first fluorescent material and a second biomolecule labeled with a second fluorescent material (S1720). In the embodiment of FIG. 17, the second biomolecule may be a biomolecule labeled with a specific fluorescent material in an (i+1)-th staining round (i.e., an (i+1)-th staining round) for the sample. That is, the first mixed image obtained in step S1710 and the second mixed image may be two images that are consecutively sequentially obtained. In other words, the first biomolecule may be a biomolecule labeled in the i staining round, and the second biomolecule may be a biomolecule labeled in the (i+1)-th staining round. The processor 110 may obtain a mixed image by obtaining the mixed image of a sample in which a second biomolecule has been labeled through a photographing unit (not illustrated) or receiving the mixed image of the sample in which a second biomolecule has been labeled from an external device or the user terminal 200.

Hereinafter, unless clearly expressed in the context, a first mixed image may denote a mixed image photographed after a first biomolecule is labeled with a first fluorescent material in an i-th staining round for a specific sample. A second mixed image may denote a mixed image photographed after a second biomolecule is labeled with a second fluorescent material in an (i+1)-th staining round for the same specific sample. The first biomolecule may be indicated on the first mixed image, and the second biomolecule may not be indicated on the first mixed image. Furthermore, both the first biomolecule and the second biomolecule may be indicated on the second mixed image.

Next, the processor 110 may generate an unmixed image of the second biomolecule based on the first mixed image and the second mixed image (S1730). In an embodiment, the processor 110 may process the first mixed image and the second mixed image based on an unmixing matrix, and may generate the unmixed image of the second biomolecule based on a result of the processing. Furthermore, a value of at least one element included in the unmixing matrix may be determined based on a trained artificial neural network model. A common description of the unmixing matrix or the artificial neural network model has been given above, and a description of redundant contents is omitted and a difference between them is described.

In an embodiment, a first mixed image and a second mixed image that are consecutively obtained with respect to the same sample may be images photographed by detecting light of the same specific wavelength band from the sample. Specifically, the first mixed image may be an image photographed by detecting light of a first wavelength band in the light emitted from the sample including a first biomolecule labeled with a first fluorescent material. The second mixed image may be an image photographed by detecting light of a second wavelength band in the light emitted from the sample including a second biomolecule labeled with a second fluorescent material. In this case, if the first wavelength band and the second wavelength band are the same, the first mixed image and the second mixed image may be images photographed by detecting light of the same specific wavelength band. In the present disclosure, the "light of a specific wavelength band" may denote light of a wavelength of a specific range. For example, the light of a specific wavelength band may denote light of a wavelength of 400 nm or more to 450 nm or less. In order to photograph a mixed image by detecting light of a specific wavelength band, a wavelength range of light detected by the photographing unit may be adjusted, light of a specific wavelength band may be radiated to a sample, or a given filter may be installed between the photographing unit and the sample.

In an embodiment, a first mixed image and a second mixed image that are sequentially obtained with respect to the same sample may be images obtained based on the same emission filter (hereinafter also referred to as a "sixth emission filter").

Figure 18:
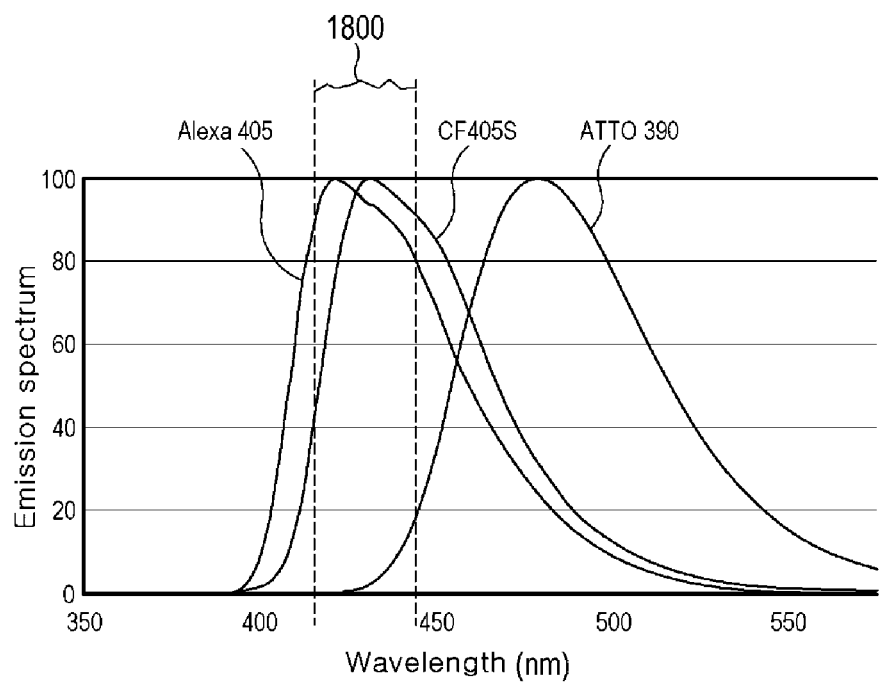
FIG. 18 is a diagram exemplarily indicating emission spectra of a plurality of fluorescent materials and wavelength bands passed by a specific emission filter.

FIG. 18 is a diagram exemplarily indicating emission spectra of a plurality of fluorescent materials and wavelength bands passed by a specific emission filter. As described above, a mixed image may be obtained by radiating, to a fluorescent material, light of a specific wavelength to which the fluorescent material responds, filtering light emitted from the fluorescent material that is excited as a result thereof through a corresponding emission filter, and photographing light passed by the emission filter. For example, it may be assumed that a first mixed image is an image obtained by labeling a first biomolecule included in a sample with one of fluorescent materials "Alexa 405", "CF405S", and "ATTO 390", and a second mixed image may be an image obtained by labeling a second biomolecule including the same sample with one of the fluorescent materials "Alexa 405", "CF405S", and "ATTO 390." In this case, the first mixed image and the second mixed image may be images obtained based on the same sixth emission filter, for example. If a wavelength band 1800 passed by a sixth emission filter is illustrated as a dotted section in FIG. 18, for example, a first mixed image and a second mixed image may be obtained by identically detecting light having the wavelength band 1800 passed by the sixth emission filter.

According to an embodiment of the present disclosure, a first fluorescent material used to obtain a first mixed image and a second fluorescent material used to obtain a second mixed image may be the same fluorescent material. For example, the first fluorescent material and the second fluorescent material may be one fluorescent material among "Alexa 405", "Alexa 488", "Alexa 546", "Alexa 647", "CF594", "CF405S", "ATTO 390", or other various fluorescent materials, and may be the same fluorescent material.

Figure 19:
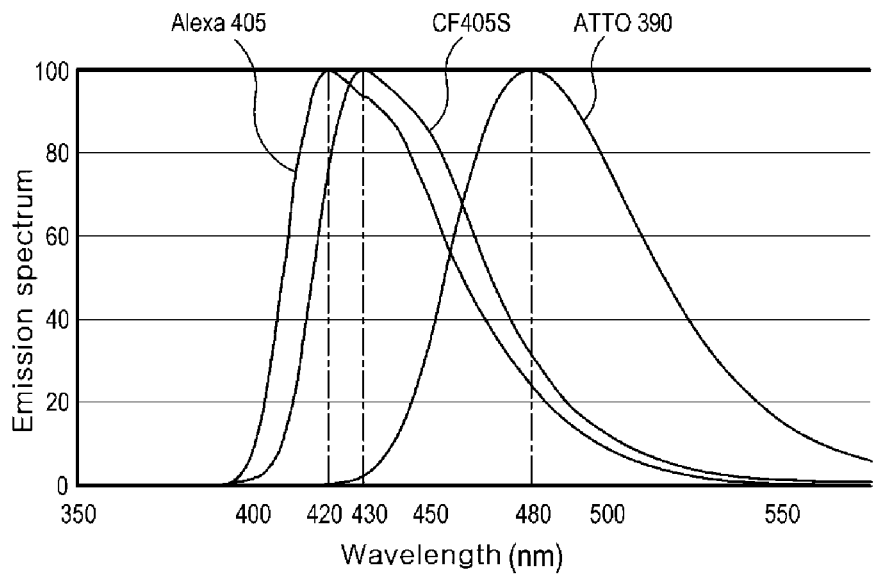
FIG. 19 is a diagram exemplarily illustrating emission spectra of a plurality of fluorescent materials and a wavelength value at which the intensity of a signal becomes a maximum in each of the emission spectra.

According to an embodiment of the present disclosure, a first fluorescent material used to obtain a first mixed image and a second fluorescent material used to obtain a second mixed image may be fluorescent materials having similar emission spectra. In the present disclosure, two or more fluorescent materials having similar emission spectra may be represented as a "fluorescent material combination having similar emission spectra." Hereinafter, a method of determining a "fluorescent material combination having similar emission spectra" is described with reference to FIG. 19. FIG. 19 is a diagram exemplarily illustrating emission spectra of a plurality of fluorescent materials and a wavelength value at which the intensity of a signal becomes a maximum in each of the emission spectra.

The processor 110 may determine a fluorescent material combination having similar emission spectra, based on the intensity of a signal within the emission spectrum of each fluorescent material. Hereinafter, it is assumed and described that a fluorescent material combination having similar emission spectra includes two fluorescent material, for convenience of description.

The processor 110 may determine two fluorescent materials as a fluorescent material combination having similar emission spectra, when a wavelength value at which the intensity of an emission signal becomes a maximum within the emission spectrum of each of the two fluorescent materials satisfies a given condition (hereinafter also referred to as a "fluorescent material combination condition"). Specifically, assuming that a first mixed image is an image photographed after a first biomolecule included in a sample is labeled with a first fluorescent material and a second mixed image is an image photographed after a second biomolecule included in the sample is labeled with a second fluorescent material, if a first wavelength value at which the intensity of an emission signal becomes a maximum within the emission spectrum of the first fluorescent material and a second wavelength value at which the intensity of an emission signal becomes a maximum within the emission spectrum of the second fluorescent material satisfy a given condition, the first fluorescent material and the second fluorescent material may correspond to a fluorescent material combination having similar emission spectra.

In an embodiment relating to a fluorescent material combination condition, the processor 110 may determine that the fluorescent material combination condition is satisfied, when each of a first wavelength value at which the intensity of an emission signal becomes a maximum within the emission spectrum of a first fluorescent material and a second wavelength value at which the intensity of an emission signal becomes a maximum within the emission spectrum of a second fluorescent material is a predetermined threshold value or less. For example, as illustrated in FIG. 19, a wavelength value at which the intensity of an emission signal becomes a maximum within the emission spectrum of "Alexa 405" (hereinafter also referred to as a "emission peak of Alexa 405") may be about 420 nm, and a wavelength value at which the intensity of an emission signal becomes a maximum within the emission spectrum of "CF405S" (hereinafter also referred to as a "emission peak of CF405S") may be about 430 nm. Furthermore, a wavelength value at which the intensity of an emission signal becomes a maximum within the emission spectrum of "ATTO 390" (hereinafter also referred to as a "emission peak of ATTO 390") may be 480 nm.

In an embodiment relating to FIG. 19, if a predetermined threshold value of the processor 110 is 20 nm, a difference between the emission peak (e.g., 420 nm) of Alexa 405 and the emission peak (e.g., 430 nm) of CF405S is 10 nm, which is the predetermined threshold value or less. Accordingly, the processor 110 may determine that Alexa 405 and CF405S satisfy the fluorescent material combination condition. In contrast, a difference between the emission peak of Alexa 405 and the emission peak (e.g., 480 nm) of ATTO 390 is 60 nm and is not the predetermined threshold value or less. Accordingly, the processor 110 may determine that Alexa 405 and ATTO 390 do not satisfy the fluorescent material combination condition. Likewise, since a difference between the emission peaks of CF405S and ATTO 390 is 50 nm, the processor 110 may determine that CF405S and ATTO 390 do not satisfy the fluorescent material combination condition.

In an embodiment relating to FIG. 19, if a predetermined threshold value of the processor 110 is 60 nm, a difference between the emission peak (e.g., 420 nm) of Alexa 405 and the emission peak (e.g., 430 nm) of CF405S is 10 nm, which is the predetermined threshold value or less. The processor 110 may determine that Alexa 405 and CF405S satisfy the fluorescent material combination condition. Furthermore, a difference between the emission peak of Alexa 405 and the emission peak (e.g., 480 nm) of ATTO 390 is 60 nm, which is the predetermined threshold value or less. Accordingly, the processor 110 may determine that Alexa 405 and ATTO 390 satisfy the fluorescent material combination condition. Likewise, since a difference between the emission peaks of CF405S and ATTO 390 is 50 nm, the processor 110 may determine that CF405S and ATTO 390 satisfy the fluorescent material combination condition. In another embodiment relating to the fluorescent material combination condition, the processor 110 may determine that the fluorescent material combination condition is satisfied, when the ratio of a smaller wavelength value to a greater wavelength value, among a first wavelength value at which the intensity of an emission signal becomes a maximum within the emission spectrum of a first fluorescent material and a second wavelength value at which the intensity of an emission signal becomes a maximum within the emission spectrum of a second fluorescent material, is a predetermined threshold ratio or more. For example, if a predetermined threshold ratio of the processor 110 is 0.95, the ratio of a smaller wavelength value to a greater wavelength value among the emission peak of Alexa 405 and the emission peak of CF405S is about 0.977 (=420/430), which is the predetermined threshold ratio or more. The processor 110 may determine that Alexa 405 and CF405S satisfy the fluorescent material combination condition. In contrast, the ratio of a smaller wavelength value to a greater wavelength value among the emission peak of Alexa 405 and the emission peak of ATTO 390 is 0.875 (=420/480), which is less than the predetermined threshold ratio. The processor 110 may determine that Alexa 405 and ATTO 390 do not satisfy the fluorescent material combination condition. Likewise, the ratio of the emission peak of each of CF405S and ATTO 390 is about 0.896 (=430/480), which is less than the predetermined threshold ratio. The processor 110 may determine that CF405S and ATTO 390 do not satisfy the fluorescent material combination condition.

Detailed numerical values of the predetermined threshold value or the predetermined threshold ratio are merely exemplary and do not limit the present disclosure. A predetermined threshold value or a predetermined threshold ratio may be set as various real number values depending on the type of fluorescent material which is used in a staining process.

According to the conventional method of processing an image which has been described with reference to FIG. 4, in order to obtain an accurate image of each of a plurality of biomolecules, fluorescent materials have to be selected so that the emission spectra of the fluorescent materials that label a plurality of biomolecules, respectively, do not overlap as much as possible. In contrast, if a plurality of unmixed images is generated from a plurality of mixed images by using the method of processing an image according to the present disclosure, such a limit of the conventional method can be greatly reduced. Moreover, in a process of consecutively obtaining mixed images by sequentially staining a plurality of biomolecules included in a sample, the same fluorescent material or similar fluorescent materials may be used for each staining round. Accordingly, in the present disclosure, a plurality of mixed images that are consecutively sequentially obtained may be obtained based on light of a specific wavelength band that is the same or similar by using methods according to the aforementioned some embodiments. Furthermore, a plurality of mixed images can be obtained more rapidly and easily compared to the conventional method without an additional process, such as the replacement of an emission filter or the removal of a fluorescent material.

In an additional embodiment according to the disclosed contents of this specification, if a plurality of mixed images is images obtained by sequentially staining a plurality of biomolecules included in a sample, an unmixing matrix may be a triangular matrix.

In an embodiment relating to a triangular matrix of the present disclosure, if a plurality of mixed images includes two mixed images, an unmixing matrix, that is, the triangular matrix, may be represented like Equation 20.

$$U = \begin{bmatrix} 1 & 0 \\ \alpha & 1 \end{bmatrix} \quad \text{[Equation 20]}$$

In Equation 20, a parameter α included in an unmixing matrix U may be a parameter for the weighted sum of mixed images. In the example of Equation 20, two mixed images may be denoted as a first mixed image $Y_1$ photographed after a first biomolecule included in a sample is labeled in an i-th staining round and a second mixed image $Y_2$ photographed after a second biomolecule included in the same sample is labeled in an (i+1)-th staining round, respectively (i is a natural number equal to or greater than 1). The processor 110 may perform an operation for obtaining an unmixed image of the second biomolecule by weighted-summing the first mixed image $Y_1$ and the second mixed image $Y_2$ by using an unmixing matrix, that is, a triangular matrix. For example, the processor 110 may operate an equation that is expressed like $X_2 = \alpha Y_1 + Y_2$ based on the unmixing matrix U of Equation 20, and may obtain an unmixed image $X_2$ of the second biomolecule based on a result of the operation. If the first mixed image $Y_1$ is an image obtained by staining the first biomolecule included in the sample in the first staining (i.e., first staining round) process for the sample, an unmixed image $X_1$ of the first biomolecule may be obtained as the first mixed image $Y_1$.

In another embodiment relating to a triangular matrix of the present disclosure, if a plurality of mixed images includes three mixed images, an unmixing matrix, that is, the triangular matrix, may be represented like Equation 21.

$$U = \begin{pmatrix} 1 & 0 & 0 \\ \alpha & 1 & 0 \\ \beta & \gamma & 1 \end{pmatrix}$$ [Equation 21]

In Equation 21, a plurality of parameters α, β, and γ included in an unmixing matrix U may be parameters for the weighted sum of mixed images, respectively. In the example of Equation 21, the three mixed images may be denoted as a first mixed image $Y_1$ photographed after a first biomolecule included in a sample is labeled in an i-th staining round, a second mixed image $Y_2$ photographed after a second biomolecule included in the same sample is labeled in an (i+1)-th staining round, and a third mixed image $Y_3$ photographed after a third biomolecule included in the same sample is labeled in the (i+1)-th staining round (i is a natural number equal to or greater than 1). The processor 110 may perform an operation for obtaining an unmixed image of the second biomolecule and an unmixed image of the third biomolecule by weighted-summing the first mixed image $Y_1$, the second mixed image $Y_2$, and the third mixed image $Y_3$ by using the unmixing matrix, that is, a triangular matrix. For example, the processor 110 may operate an equation which is expressed like $X_2 = \alpha Y_1 + Y_2$ and $X_3 = \beta Y_1 + \gamma Y_2 + Y_3$ based on the unmixing matrix U of Equation 21, and may obtain an unmixed Image $X_2$ of the second biomolecule and an unmixed image $X_3$ of the third biomolecule as a result of the operation. If the first mixed image $Y_1$ is an image obtained after the first biomolecule included in the sample is labeled in the first staining (i.e., the first round staining) process for the sample, an unmixed image $X_1$ of the first biomolecule may be obtained as the first mixed image $Y_1$.

In the detailed description based on Equations 20 and 21, the triangular matrix as the unmixing matrix has been described as a lower triangular matrix, but does not limit the present disclosure and the triangular matrix of the present disclosure may be an upper triangular matrix. If a plurality of mixed images is images obtained by sequentially staining a plurality of biomolecules included in a sample as described above, the unmixing matrix according to the present disclosure may be a triangular matrix. Accordingly, the processor 110 can obtain an unmixed image of at least one biomolecule by performing a matrix operation more rapidly.

In the flowchart or flow diagram according to the disclosed contents of this specification, each of the steps of the method or algorithm has been described in a sequential order, but the steps may be performed in an order in which the steps may be randomly combined in addition to the sequential execution. The description of the flowchart of flow diagram of this specification does not limit a change in or a modification for the method or algorithm, and does not mean that a given step is essential or preferred. In an embodiment, at least some steps may be performed in parallel, iteratively or heuristically. In an embodiment, at least some step may be omitted or another step may be added.

Various embodiments according to the disclosed contents of this specification may be implemented as software in a machine-readable storage medium. The software may be software for implementing various embodiments of this specification. The software may be inferred from various embodiments of this specification by programmers in the technical field to which the disclosed contents of this specification pertain. For example, the software may be a program a machine-readable instruction (e.g., a code or a code segment). A device is a device which may operate in response to an instruction invoked from a storage medium, and may be a computer, for example. In an embodiment, a device may be a computing device according to various embodiments of this specification. In an embodiment, a processor of the device may execute an invoked instruction so that components of the device may perform a function corresponding to the invoked instruction. In an embodiment, the processor may be the processor 110, 210 according to the embodiments of this specification. The storage medium may mean all types of recording media which may be read by the device and in which data is stored. The storage medium may include ROM, RAM, CD-ROM, a magnetic tape, a floppy disk, and an optical data storage device, for example. In an embodiment, the storage medium may be the memory 130, 230. In an embodiment, the storage medium may be implemented in a form distributed to computer systems that are connected over a network. The software may be distributed, stored, and executed in computer systems. The storage medium may be a non-transitory storage medium. The non-transitory storage medium means a tangible medium regardless of data being semi-permanently or temporarily stored, and does not include a signal that is transitorily propagated.

Although the technical spirit according to the disclosed contents of this specification has been described through various embodiments, the technical spirit of the disclosed contents of this specification includes various substitutions, modifications, and changes which may be performed in a range which may be understood by a person having ordinary knowledge in the technical field to which the disclosed contents of this specification pertain. Furthermore, it should be understood that such substitutions, modifications, and changes may be included in the appended claims.

What is claimed is:

1. A method of processing an image, which is performed by an electronic device comprising one or more processors and one or more memories in which instructions to be executed by the one or more processors are stored, the method comprising:
    obtaining a first mixed image of a sample comprising a first biomolecule labeled with a first fluorescent material and a second biomolecule that has not been labeled;
    obtaining a second mixed image of the sample comprising the first biomolecule labeled with the first fluorescent material and the second biomolecule labeled with a second fluorescent material;
    obtaining a third mixed image of the sample comprising the first biomolecule labeled with the first fluorescent material, the second biomolecule labeled with the second fluorescent material, and a third biomolecule labeled with a third fluorescent material; and
    generating an unmixed image of the second biomolecule based on the first mixed image and the second mixed image,
    wherein the generating of the unmixed image comprises generating an unmixed image of the third biomolecule additionally based on the third mixed image,
    wherein the first mixed image is an image obtained by photographing a sample comprising the second biomolecule that has not been labeled and the third biomolecule that has not been labeled,
    wherein the second mixed image is an image obtained by photographing a sample comprising the third biomolecule that has not been labeled.

2. The method of claim 1, wherein the first mixed image and the second mixed image are images photographed by detecting light of an identical specific wavelength band from the sample.

3. The method of claim 1, wherein the first mixed image and the second mixed image are images obtained based on an identical emission filter, and wherein the emission filter transmits light of a specific wavelength band.

4. The method of claim 1, wherein the first fluorescent material and the second fluorescent material are an identical fluorescent material.

5. The method of claim 1, wherein the first fluorescent material and the second fluorescent material are determined so that a first wavelength value at which an intensity of an emission signal becomes a maximum within an emission spectrum of the first fluorescent material and a second wavelength value at which the intensity of an emission signal becomes a maximum within an emission spectrum of the second fluorescent material satisfy a given condition.

6. The method of claim 5, wherein the given condition is a condition that is satisfied when a difference value between the first wavelength value and the second wavelength value is a predetermined threshold value or less.

7. The method of claim 5, wherein the given condition is a condition that is satisfied when a ratio of a smaller wavelength value to a greater wavelength value, among the first wavelength value and the second wavelength value, is a predetermined threshold ratio or more.

8. The method of claim 1, wherein the second mixed image is obtained by staining the second biomolecule comprised in the sample with the second fluorescent material and then photographing the sample, after the first mixed image of the sample is photographed.

9. The method of claim 1, wherein the generating of the unmixed image comprises processing the first mixed image and the second mixed image by using an unmixing matrix.

10. The method of claim 9, wherein a value of at least one element included in the unmixing matrix is determined based on a trained artificial neural network model.

11. The method of claim 1, wherein the second mixed image is obtained by staining the second biomolecule included in the sample with the second fluorescent material and then photographing the sample, after the first mixed image of the sample is photographed, and
wherein the third mixed image is obtained by staining the third biomolecule included in the sample with the third fluorescent material and then photographing the sample, after the second mixed image of the sample is photographed.

12. An electronic device comprising:
one or more processors; and
one or more memories in which instructions to be executed by the one or more processors are stored,
wherein the one or more processors
obtain a first mixed image of a sample comprising a first biomolecule labeled with a first fluorescent material and a second biomolecule that has not been labeled;
obtain a second mixed image of the sample comprising the first biomolecule labeled with the first fluorescent material and the second biomolecule labeled with a second fluorescent material;
obtain a third mixed image of the sample comprising the first biomolecule labeled with the first fluorescent material, the second biomolecule labeled with the second fluorescent material, and a third biomolecule labeled with a third fluorescent material, and
generate an unmixed image of the second biomolecule based on the first mixed image and the second mixed image,
wherein the generating of the unmixed image comprises generating an unmixed image of the third biomolecule additionally based on the third mixed image,
wherein the first mixed image is an image obtained by photographing a sample comprising the second biomolecule that has not been labeled and the third biomolecule that has not been labeled, and
wherein the second mixed image is an image obtained by photographing a sample comprising the third biomolecule that has not been labeled.

13. The electronic device of claim 12, wherein the first mixed image and the second mixed image are images photographed by detecting light of an identical specific wavelength band from the sample.

14. The electronic device of claim 12, wherein the first mixed image and the second mixed image are images obtained based on an identical emission filter, and wherein the emission filter transmits light of a specific wavelength band.

15. The electronic device of claim 12, wherein the first fluorescent material and the second fluorescent material are an identical fluorescent material.

16. The electronic device of claim 12, wherein the first fluorescent material and the second fluorescent material are determined so that a first wavelength value at which an intensity of an emission signal becomes a maximum within an emission spectrum of the first fluorescent material and a second wavelength value at which the intensity of an emission signal becomes a maximum within an emission spectrum of the second fluorescent material satisfy a given condition.

17. The electronic device of claim 12, wherein the second mixed image is obtained by staining the second biomolecule included in the sample with the second fluorescent material and then photographing the sample, after the first mixed image of the sample is photographed.

18. The electronic device of claim 12, further comprising a photographing unit,
wherein the one or more processors
obtain the first mixed image by photographing the sample comprising the first biomolecule labeled with the first fluorescent material and the second biomolecule that has not been labeled through the photographing unit, and
obtain the second mixed image by photographing the sample comprising the first biomolecule labeled with the first fluorescent material and the second biomolecule labeled with a second fluorescent material through the photographing unit.

19. A non-transitory computer-readable recording medium on which upon execution by one or more processors, instructions enabling the one or more processors to perform an operation are recorded,
wherein the instructions enable the one or more processors to perform a method of processing an image comprising:
obtaining a first mixed image of a sample comprising a first biomolecule labeled with a first fluorescent material and a second biomolecule that has not been labeled,
obtaining a second mixed image of the sample comprising the first biomolecule labeled with the first fluorescent material and the second biomolecule labeled with a second fluorescent material, and generating an unmixed image of the second biomolecule based on the first mixed image and the second mixed image, obtaining a third mixed image of the sample comprising the first biomolecule labeled with the first fluorescent material, the second biomolecule labeled with the second fluorescent material, and a third biomolecule labeled with a third fluorescent material, wherein the generating of the unmixed image comprises generating an unmixed image of the third biomolecule additionally based on the third mixed image, wherein the first mixed image is an image obtained by photographing a sample comprising the second biomolecule that has not been labeled and the third biomolecule that has not been labeled, and wherein the second mixed image is an image obtained by photographing a sample comprising the third biomolecule that has not been labeled.

* * * * *